United States Patent
Cong et al.

(10) Patent No.: US 10,489,942 B2
(45) Date of Patent: Nov. 26, 2019

(54) DEVICES, SYSTEMS AND METHODS UTILIZING FRAMELET-BASED ITERATIVE MAXIMUM-LIKELIHOOD RECONSTRUCTION ALGORITHMS IN SPECTRAL CT

(71) Applicants: University of Iowa Research Foundation, Iowa City, IA (US); Shandong University, Licheng, Shandong (CN); Shandong Provincial Chest Hospital, Shandong, Shen (CN); Rensselaer Polytechnic Institute, Troy, NY (US)

(72) Inventors: Wenxiang Cong, Troy, NY (US); Ye Yangbo, Coralville, IA (US); Ge Wang, Troy, NY (US); Shuwei Mao, Jinan (CN); Yingmei Wang, Jinan (CN)

(73) Assignees: RENSSELAER POLYTECHNIC INSTITUTE, Troy, NY (US); SHANDONG UNIVERSITY, Jinan, Licheng, Shandong (CN); SHANDONG PROVINCIAL CHEST HOSPITAL, Lixia Qu, Jinan Shi, Shandong Shen (CN); UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 16/087,419

(22) PCT Filed: Mar. 23, 2017

(86) PCT No.: PCT/US2017/023851
§ 371 (c)(1),
(2) Date: Sep. 21, 2018

(87) PCT Pub. No.: WO2017/165672
PCT Pub. Date: Sep. 28, 2017

(65) Prior Publication Data
US 2019/0102918 A1 Apr. 4, 2019

Related U.S. Application Data

(60) Provisional application No. 62/312,316, filed on Mar. 23, 2016.

(51) Int. Cl.
*G06T 11/00* (2006.01)
*A61B 6/03* (2006.01)

(52) U.S. Cl.
CPC ............ *G06T 11/006* (2013.01); *A61B 6/032* (2013.01); *G06T 11/003* (2013.01);
(Continued)

(58) Field of Classification Search
CPC ..... A61B 6/032; G06T 11/005; G06T 11/006; G06T 2211/408; G06T 2211/424; G06T 11/003
See application file for complete search history.

(56) References Cited

U.S. PATENT DOCUMENTS 7,187,745 B2 *  3/2007 Flohr ................... A61B 5/0452
                                                         378/62
8,879,814 B2 * 11/2014 Wollenweber ......... A61B 6/032
                                                         382/131
(Continued)

FOREIGN PATENT DOCUMENTS

WO         2014203151 A1    6/2014

OTHER PUBLICATIONS

Wang et al. ("Fast gradient-based algorithm for total variation regularized tomography reconstruction," 2011 4th International Congress on Image and Signal Processing, vol. 3, 2011) (Year: 2011).*

(Continued)

*Primary Examiner* — Yubin Hung
(74) *Attorney, Agent, or Firm* — Matthew Warner-Blankenship; Davis, Brown, Koeln, Shors & Roberts, P.C.

(57) ABSTRACT

The disclosed apparatus, systems and methods relate to a framelet-based iterative algorithm for polychromatic CT (Continued)

which can reconstruct two components using a single scan. The algorithm can have various steps including a scaled-gradient descent step of constant or variant step sizes; a non-negativity step; a soft thresholding step; and a color reconstruction step.

14 Claims, 13 Drawing Sheets

(52) U.S. Cl.
CPC ....... *G06T 11/005* (2013.01); *G06T 2211/408* (2013.01); *G06T 2211/424* (2013.01)

(56) References Cited

U.S. PATENT DOCUMENTS

| | | | |
|---|---|---|---|
| 9,865,060 B2* | 1/2018 | Mukumoto | A61B 6/5205 |
| 2003/0156684 A1 | 8/2003 | Fessler | |
| 2009/0003721 A1 | 1/2009 | Karidi | |
| 2009/0262997 A1 | 10/2009 | Zou et al. | |
| 2011/0044546 A1* | 2/2011 | Pan | G06T 11/006 382/195 |
| 2012/0155728 A1 | 6/2012 | DeMan et al. | |
| 2012/0265050 A1 | 10/2012 | Wang | |
| 2014/0307067 A1* | 10/2014 | Douglas | H04N 13/363 348/53 |
| 2015/0030227 A1* | 1/2015 | Liang | G06T 11/006 382/131 |

OTHER PUBLICATIONS

Sidky et al. ("Analysis of iterative region-of-interest image reconstruction for x-ray computed tomography," Journal of Medical Imaging 1 (3), Oct. 3, 2014) (Year: 2014).*

Sidky et al. ("Accurate image reconstruction from few-views and limited-angle data in divergent-beam CT," Journal of X-ray science and technology, 14(2), 2006) (Year: 2006).*

Chamorro-Servent et al. ("Use of Split Bregman denoising for iterative reconstruction in fluorescence diffuse optical tomography," Journal of Biomedical Optics 18 (7), Jul. 17, 2013) (Year: 2013).*

Alvarez et al., "Energy-selective reconstructions in x-ray computerized tomography", "Physics in Medicine and Biology", 1976, pp. 733-744, vol. 21, No. 5.

Avrin et al., "Clinical application of Compton and photoelectric reconstruction in computed tomography: preliminary results", "Investigative Radiology", 1978, pp. 217-222, vol. 13, No. 3.

Brooks et al., "Beam hardening in x-ray reconstructive tomography", "Physics in Medicine and Biology", 1976, pp. 54-57, vol. 4, No. 1.

Cai et al., "A framelet-based image inpainting algorithm", "Applied and Computational Harmonic Analysis", 2008, pp. 131-149, vol. 24, No. 2.

Cai et al., "Image restoration: Total variation, wavelet frames, and beyond", "Journal of the American Mathematical Society", 2012, pp. 1033-1089, vol. 25, No. 4.

Cai et al., "Split Bregman methods and frame based image restoration", "Multiscale modeling & simulation", 2009, pp. 337-369, vol. 8, No. 2.

Chen et al., "Prior image constrained compressed sensing (PICCS): a method to accurately reconstruct dynamic ct images from highly undersampled projection data sets.", "Medical Physics", 2008, pp. 660-663, vol. 35, No. 2.

Christ, "Exact treatment of the dual-energy method in CT using polyenergetic X-ray spectra", "Physics in Medicine and Biology", 1984, pp. 1501-1510, vol. 29, No. 12.

Chu et al., "Combination of current-integrating/photon-counting detector modules for spectral CT", "Physics in Medicine and Biology", 2013, p. 7009 vol. 58, No. 19.

Daubechies et al., "Framelets: MRA-based construction of wavelet frames", "Applied and Computational Harmonic Analysis,", 2003, pp. 1-46, vol. 14, No. 1.

De Man et al., "Metal streak artifacts in X-ray computed tomography: a simulation study. In Nuclear Science Symposium", "Conference Record. 1998 IEEE", 1998, pp. 1860-1865, vol. 3.

De Man et al., "Reduction of metal streak artifacts in x-ray computed tomography using a transmission maximum a posteriori algorithm", "IEEE Transactions on Nuclear Science", 2000, pp. 977-981, vol. 47, No. 3.

Fessler et al., "Maximum-likelihood dual-energy tomographic image reconstruction in Medical Imaging", "International Society for Optics and Photonics", 2002, pp. 38-49.

Fleischmann et al., "Computed tomographyold ideas and new technology", "European Radiology", 2011, pp. 510-517, vol. 21, No. 3.

Gao et al., "Multi-energy CT based on a prior rank, intensity and sparsity model (PRISM).", "Inverse Problems", 2011, p. 115012, vol. 27, No. 11.

GE Healthcare, "Computed TomographyRevolution HD", "http://www3.gehealthcare.com/en/products/categories/computed_tomography/revolution_hd.".

Goldstein et al., "The split Bregman method forL_1-regularized problems", "SIAM Journal on Imaging Sciences", 2009, pp. 323-343, vol. 2, No. 2.

He et al., "Energy-discriminative performance of a spectral micro-CT system", "Journal of X-ray Science and Technology,", 2013, vol. 21, No. 3.

He, "Optimization of K-edge imaging with spectral CT", "Medical Physics", 2012, pp. 6572-6579, vol. 39, No. 11.

Hemmingsson et al., "Dual energy computed tomography: simulated monoenergetic and material-selective imaging", "Journal of Computer Assisted Tomography", 1986, pp. 490-499, vol. 10, No. 3.

Herman, "Correction for beam hardening in computed tomography", "Physics in Medicine and Biology", 1979, pp. 81-106, vol. 24, No. 1.

Hounsfield, "Computerized transverse axial scanning (tomography): Part 1. Description of system", "The British Journal of Radiology", 1973, pp. 1016-1022, vol. 46, No. 552.

Hsieh, "Adaptive streak artifact reduction in computed tomography resulting from excessive x-ray photon noise", "Medical Physics", 1998, pp. 2139-2147, vol. 25, No. 11.

Hudson et al., "Accelerated image reconstruction using ordered subsets of projection data", "IEEE Transactions on Medical Imaging", 1994, pp. 601-609, vol. 13, No. 4.

Joseph et al., "A method for correcting bone induced artifacts in computed tomography scanners", "Journal of Computer Assisted Tomography", 1978, pp. 623-626, vol. 2, No. 1.

Joseph et al., "A method for simultaneous correction of spectrum hardening artifacts in CT images containing both bone and iodine", "Medical Physics", 1997, pp. 1629-1634, vol. 24, No. 10.

Lange et al., "EM reconstruction algorithms for emission and transmission tomography", "Journal of Computer Assisted Tomography", 1984, pp. 306-316, vol. 8, No. 2.

Li et al., "Spectral CT modeling and reconstruction with hybrid detectors in dynamic-threshold-based counting and integrating modes", "IEEE Transactions on Medical Imaging", 2015, pp. 716-728, vol. 34, No. 3.

Man et al., "An iterative maximum-likelihood polychromatic algorithm for CT", "IEEE Transactions on Medical Imaging", 2001, pp. 999-1008, vol. 20, No. 10.

McDavid et al., "Correction for spectral artifacts in cross-sectional reconstruction from x rays", "Medical Physics", 1977, pp. 54-27, vol. 4, No. 1.

Mumcuoglu et al., "Fast gradient-based methods for Bayesian reconstruction of transmission and emission PET images", "IEEE Transactions on Medical Imaging", 1994, pp. 687-701, vol. 13, No. 4.

Natterer, "The mathematics of computerized tomography", 1986, vol. 32, Publisher: Siam.

(56) References Cited

OTHER PUBLICATIONS

Nuyts et al., "Iterative reconstruction for helical CT: a simulation study", "Physics in Medicine and Biology,", 1998, pp. 729-737, vol. 43, No. 4.

Pang et al., "Corrections for X-ray polychromaticity effects on three dimensional reconstruction", "IEEE Transactions on Biomedical Engineering,", 1976, pp. 623-626, vol. 23, No. 1.

Phelps et al., "Attenuation coefficients of various body tissues, fluids, and lesions at photon energies of 18 to 136 keV 1", "Radiology", 1975, pp. 573-583, vol. 117, No. 3.

Ron et al., "A maximum likelihood approach to emission image reconstruction from projections.", "IEEE Transactions on Nuclear Science", 1976, pp. 1428-1432, vol. 23, No. 4.

Ron et al., "The analysis of the analysis operator. Journal of Functional Analysis", "Journal of Functional Analysis", 1997, pp. 408-447, vol. 148, No. 2.

Schirra et al., "Statistical reconstruction of material decomposed data in spectral CT", "IEEE Transactions on Medical Imaging", 2013, pp. 1249-1257, vol. 32, No. 7.

Silva et al., "Innovations in CT dose reduction strategy: application of the adaptive statistical iterative reconstruction algorithm", "American Journal of Roentgenology", 2010, pp. 191-199, vol. 194, No. 1.

Stonestrom et al., "A framework for spectral artifact corrections in X-ray CT", "IEEE Transactions on Biomedical Engineering", 1981, pp. 128-141, vol. 2.

Xu et al., "Image reconstruction for hybrid true-color micro-CT", "IEEE Transactions on Biomedical Engineering", 2012, pp. 1711-1719, vol. 59, No. 6.

Yan et al., "Reconstruction algorithm for polychromatic CT imaging: application to beam-hardening correction", "IEEE Transactions on Medical Imaging,", 2000, pp. 1-11, vol. 19, No. 1.

Yang et al., "A new method to determine the center of rotation shift in 2D-CT scanning system using image cross correlation", "NDT & E International", 2012, pp. 48-54, vol. 46.

Yang et al., "Center of rotation automatic measurement for fan-beam CT system based on sinogram image features", "Neurocomputing", 2013, pp. 250-257, vol. 120.

Yang et al., "Extra projection data identification method for fast-continuous-rotation industrial cone-beam CT", "Journal of X-ray Science and Technology", 2013, pp. 467-479, vol. 21, No. 4.

Yu et al., "Compressed sensing based interior tomography", "Physics in Medicine and Biology", 2009, pp. 2791-2805, vol. 54, No. 9.

Zhao et al., "Dual-dictionary learning-based iterative image reconstruction for spectral computed tomography application", "Physics in Medicine and Biology", 2012, pp. 8217-8229, vol. 57, No. 24.

\* cited by examiner

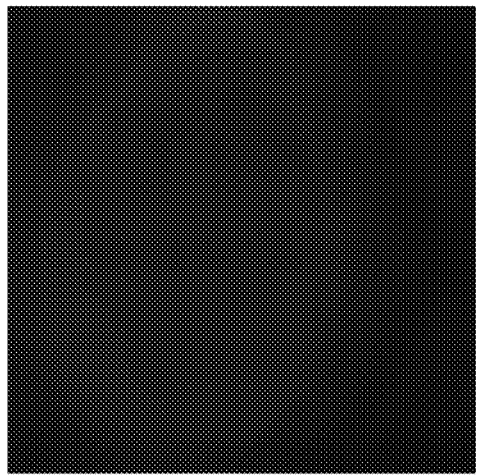
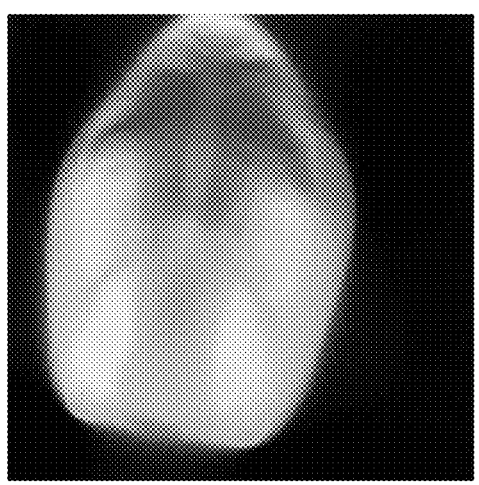
FIG. 11A  FIG. 11B
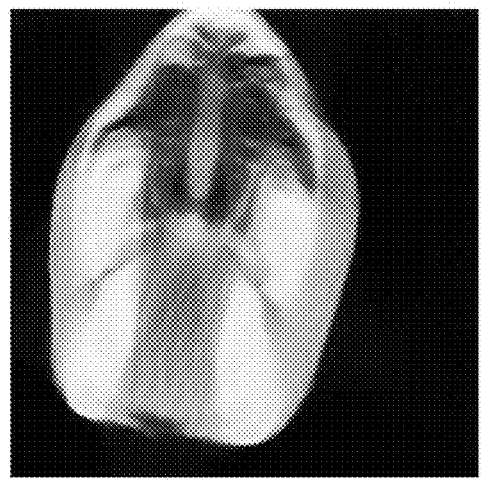
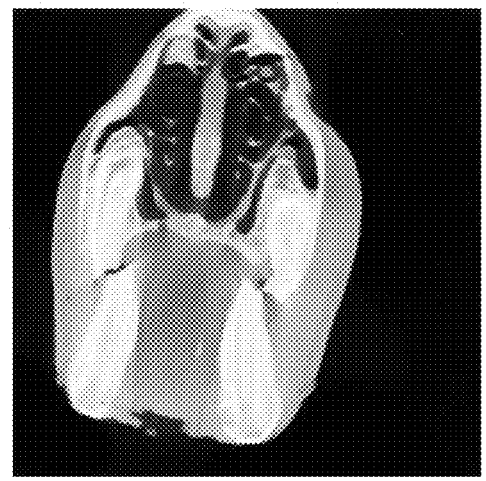
FIG. 11C  FIG. 11D

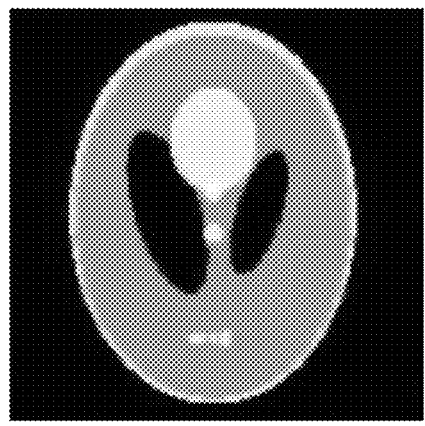
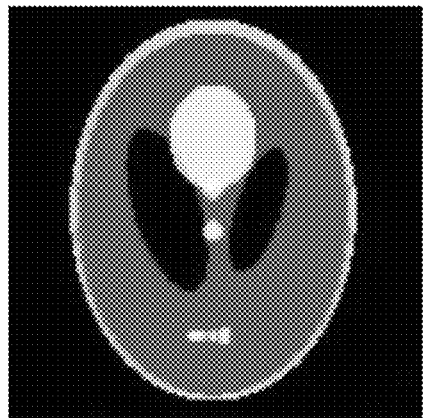
FIG. 13A  FIG. 13B
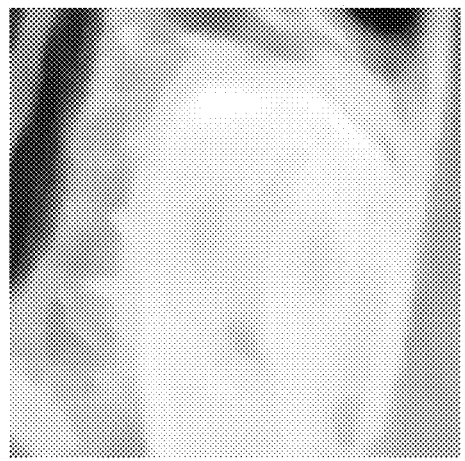
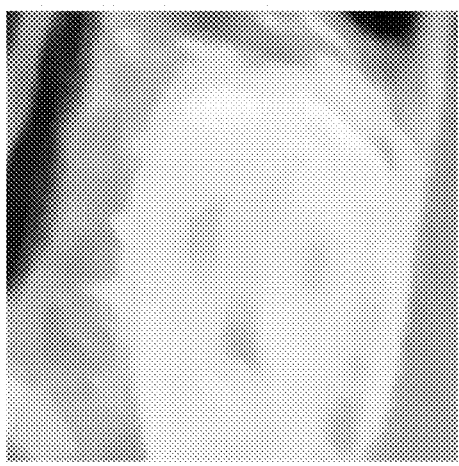
FIG. 14A  FIG. 14B

DEVICES, SYSTEMS AND METHODS UTILIZING FRAMELET-BASED ITERATIVE MAXIMUM-LIKELIHOOD RECONSTRUCTION ALGORITHMS IN SPECTRAL CT

CROSS-REFERENCE TO RELATED APPLICATION(S)

This application is a U.S. national stage application under 35 U.S.C. 371 and claims priority to International PCT Application No. PCT/US17/23851 filed Mar. 23, 2017, which claims priority to U.S. Provisional Application No. 62/312,316 filed Mar. 23, 2016, both of which are entitled "Devices, Systems and Methods Utilizing Framelet-Based Iterative Maximum-Likelihood Reconstruction Algorithms in Spectral CT," and are hereby incorporated by reference in their entirety under 35 U.S.C. § 119(e).

GOVERNMENT SUPPORT

This invention was made with government support under Grant Nos. R01 EB016977 and U01 EB017140, awarded by the National Institutes of Health. The government has certain rights in the invention.

TECHNICAL FIELD

The disclosure relates to devices, systems and methods relating to the acquisition and processing of CT images. Namely, various disclosed implementations feature a three-step iterative algorithm based on maximum likelihood and sparse representation and reconstructs images with spectral information from only one scan on a standard energy-integrating detector.

BACKGROUND

Since the introduction of X-ray computed tomography ("CT") in 1972, it has become apparent that low-energy photons are absorbed by the body more readily than high-energy photons. This differential in absorption is known in the art as the "hard-beam effect," and presents several limitations. The implementation of spectral CT has become an area of focus in counteracting the hard-beam effect.

Various hardware systems have been developed to implement spectral CT. For example, in dual-energy CT, a CT machine (such as a GE Discovery CT750 HD) scans an object with two distinct energy spectra. Dual-energy CT machines are rare and costly. Another strategy is to use a single X-ray spectrum but with energy-discriminative detectors to capture responses at different energies, and the data is processed using spectral CT iterative reconstruction algorithms. Others have attempted to improve the hardware of CT machines to reduce hard-beam artifacts, through methods such as pre-filtering the X-ray beam.

Several software approaches have also been developed. Early attempts sought to reduce beam-hardening streak artifacts, and the idea of spectral CT emerged. An iterative maximum-likelihood polychromatic algorithm for CT ("IMPACT") was developed. IMPACT seeks to find the attenuation coefficient distribution that maximizes the log-likelihood function. It was demonstrated that the IMPACT algorithm is good at eliminating beam-hardening artifacts, and it can be applied in reducing metal artifacts. The use of a filtered back projection ("FBP") reconstruction algorithms has been the most popular method of reconstructing CT images. In the FBP reconstruction algorithm, a linear attenuation coefficient is reconstructed. In these applications, it is assumed that the linear attenuation coefficient is energy-independent.

However, as discussed above, when X-rays penetrate the human body, low-energy photons are more readily absorbed than high-energy photons. In particular, linear attenuation coefficients reconstructed by the FBP algorithm tend to have a poor contrast resolution for low-density soft tissues and therefore yield poor results in the diagnosis of challenging lesions. Many iterative FBP reconstruction algorithms have also been introduced since the first commercial CT scanner was developed in 1972. Typically, these prior art iterative algorithms also suffer from the hard-beam effect because the spectrum of X-rays is ignored in computing the underlying attenuation coefficients.

Finally, many practitioners utilizing FBP and other reconstruction algorithms inject iodine contrast material into the blood to address the hard-beam effect. However, an iodine injection can cause medical complications and increase costs, and therefore does not present an ideal spectral CT solution.

There is a need in the art for improved systems and methods for the implementation of spectral CT. Unlike the hardware improvements discussed above, the disclosed embodiments can realize spectral CT by implementing iterative algorithms on existing CT hardware platforms.

BRIEF SUMMARY

Dual-energy or multi-energy CT can produce spectral information of an object. It uses either two scans, one for lower-energy and the other for higher energy X-ray, or one scan using an energy-discriminative detector. The presently-disclosed examples and implementations utilize an algorithm capable of reconstructing an image with spectral information from just one scan through data from a current energy-integrating detector. Accordingly, color CT images can be created by merging reconstructed images at multiple energy levels or by an adaptive color fusion method.

In these embodiments, the spectral curves of the attenuation coefficient $\mu(r,E)$ can be established and analyzed at any point in the scanned object. These spectral curves present a valuable tool in diagnosing the nature of a tumor, including soft, difficult lesions. Further, the presently disclosed system and methods do not require new CT hardware: existing machines can be used. The disclosed systems and methods utilize an algorithm generating a sparse representation in a framelet system. The various implementations of the disclosed algorithm are based on a polychromatic acquisition model for X-ray CT, where the linear attenuation coefficients (designated $\mu$) are energy-dependent. One advantage of the presently disclosed implementations is that practitioners can reduce the use of iodine by accounting for the continuous spectrum information of X-rays. These implementations can also provide more detailed anatomical information.

Described herein are various embodiments relating to devices, systems and methods for reconstructing CT images. Although multiple embodiments, including various devices, systems, and methods of generating these images are described herein as an "algorithm," this is in no way intended to be restrictive to a specific modality, implementation or embodiment.

In Example 1, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method for reconstructing a polychromatic CT image from a single scan, including providing a computer implementing a computer-readable media and implementing a framelet-based iterative algorithm including a scaled-gradient descent step, a non-negativity step, and a soft thresholding step. Other embodiments of this aspect include corresponding computer systems, apparatus, and computer programs recorded on one or more computer storage devices, each configured to perform the actions of the methods. In certain embodiments, a system may be provided that includes a processing device and a non-transitory computer-readable medium accessible by the processing device. The processing device may be configured to execute logic embodied in the non-transitory computer-readable medium to reconstruct the discussed images from a single CT scan.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes A system for reconstructing a polychromatic CT image from a single scan using energy-dependent attenuation coefficients, including: a computer implementing a computer-readable media including the single CT scan; and an analysis unit executing a computer program configured for implementing a framelet-based iterative algorithm for CT image reconstruction including: a scaled-gradient descent step; a non-negativity step; and a soft thresholding step. Other embodiments of this aspect include corresponding computer systems, apparatus, and computer programs recorded on one or more computer storage devices, each configured to perform the actions of the methods.

Implementations may include one or more of the following features. The system where the soft thresholding step includes constant or variant thresholding sizes. The system where the scaled-gradient descent step includes constant or variant step sizes. The system where the framelet-based iterative algorithm further includes a color reconstruction step. The system further including a CT platform. The system where the soft thresholding step is configured to promote sparsity in the framelet domain. The system where the during non-negativity step, any negative components are set to 0 to maintain positivity of attenuation coefficients σ, θ. The system where the color reconstruction step further includes an adaptive color fusion method. The system where the reconstructed CT image is interior spectral CT The system where the reconstructed CT image is global spectral CT. The system where $\phi=\phi(r)$ defines a photoelectric component and $\theta=\theta(r)$ defines a Compton scatter component of the attenuation coefficient $\mu(r,E)$ at each point r. The system where the iterative algorithm includes iterating on n as follows:

$$\phi_j^{n+\frac{1}{3}} = \phi_j^n - \delta_1 \frac{\partial L}{\partial \phi_j}(\phi^n, \theta^n) \left( \sum_{h=1}^{j} \left( \frac{\partial^2 L}{\partial \phi_j \partial \phi_h} + \frac{\partial^2 L}{\partial \phi_j \partial \theta_h} \right)(\phi^n, \theta^n) \right)^{-1}$$

$$\phi_j^{n+\frac{2}{3}} = \max\left\{\phi_j^{n+\frac{1}{3}}, 0\right\}$$

-continued $$\theta_j^{n+\frac{1}{3}} = \theta_j^n - \delta_2 \frac{\partial L}{\partial \theta_j}(\phi^n, \theta^n) \left( \sum_{h=1}^{j} \left( \frac{\partial^2 L}{\partial \theta_j \partial \phi_h} + \frac{\partial^2 L}{\partial \theta_j \partial \theta_h} \right)(\phi^n, \theta^n) \right)^{-1}$$

$$\theta_j^{n+\frac{2}{3}} = \max\left\{\theta_j^{n+\frac{1}{3}}, 0\right\}$$

$$\phi_j^{n+1} = W^T T_{\lambda_1}\left(W \phi_j^{n+\frac{2}{3}}\right)$$

$$\theta_j^{n+1} = W^T T_{\lambda_2}\left(W \theta_j^{n+\frac{2}{3}}\right).$$

The system where the system is configured to assign RGB components to obtain a color image. The system further including an adaptive color fusion method. The system where the adaptive color fusion method is based on a singular value decomposition. The system further including a tight frame system with wavelet structure. The system where the non-negativity step is configured to reset negative values to zero at each point r to promote processing. The system further including a CT platform configured to generate a single polychromatic scan. Implementations of the described techniques may include hardware, a method or process, or computer software on a computer-accessible medium.

One general aspect includes A single scan polychromatic CT image reconstruction system, including: a computer implementing a computer-readable media including a single CT scan; and a processor configured to implement a framelet-based iterative algorithm configured for implementing a framelet-based iterative algorithm for CT image reconstruction from the single CT scan, the iterative algorithm including: a scaled-gradient descent step of constant or variant step sizes; a non-negativity step; a soft thresholding step; and a reconstruction step, where the processor is configured to reconstruct the CT image following the execution of the iterative steps. Other embodiments of this aspect include corresponding computer systems, apparatus, and computer programs recorded on one or more computer storage devices, each configured to perform the actions of the methods.

Implementations may include one or more of the following features. The system where the color reconstruction step further includes an adaptive color fusion method. The system where the reconstructed CT image is interior spectral CT The system where the reconstructed CT image is global spectral CT. The system where $\phi=\phi(r)$ defines a photoelectric component and $\theta=\theta(r)$ defines a Compton scatter component of the attenuation coefficient $\mu(r,E)$ at each point r. The system where the system is configured to assign RGB components to obtain a color image. The system further including an adaptive color fusion method. The system where the adaptive color fusion method is based on a singular value decomposition. The system further including a tight frame system with wavelet structure. The system where the non-negativity step is configured to reset negative values to zero at each point r to promote processing. The system further including a CT platform configured to generate a single polychromatic scan. Implementations of the described techniques may include hardware, a method or process, or computer software on a computer-accessible medium.

One general aspect includes A system for reconstructing a polychromatic CT image from a single CT scan using energy-dependent attenuation coefficients, including: at least one x-ray tube; at least one detector configured to receive x-rays from the at least one x-ray tube; the single CT scan generated by the at least one detector; and an analysis unit operably coupled to the at least one detector, the analysis unit including a computer program configured for implementing a framelet-based iterative algorithm for CT image reconstruction from the single CT scan, the iterative algorithm including: a non-negativity step such that negative components are set to zero to force attenuation coefficient positivity; a soft thresholding step on framelet coefficients to impose image framelet domain sparsity; and a scaled-gradient descent step to decrease the $l_2$-norm error. Other embodiments of this aspect include corresponding computer systems, apparatus, and computer programs recorded on one or more computer storage devices, each configured to perform the actions of the methods.

Implementations may include one or more of the following features. The system further including an adaptive color fusion method. The system where the adaptive color fusion method is based on a singular value decomposition. The system further including a tight frame system with wavelet structure. The system where the non-negativity step is configured to reset negative values to zero at each point r to promote processing. The system further including a CT platform configured to generate a single polychromatic scan. Implementations of the described techniques may include hardware, a method or process, or computer software on a computer-accessible medium.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 11A depicts a reconstructed attenuation coefficients $\mu(r,E)$ with an overlay for global spectral CT at monochromatic E=40, 70, 100 keV for 1 iteration, according to one embodiment.

FIG. 11B depicts a reconstructed attenuation coefficients $\mu(r,E)$ with an overlay for global spectral CT at monochromatic E=40, 70, 100 keV for 10 iterations, according to one embodiment.

FIG. 11C depicts a reconstructed attenuation coefficients $\mu(r,E)$ with an overlay for global spectral CT at monochromatic E=40, 70, 100 keV for 40 iterations, according to one embodiment.

FIG. 11D depicts a reconstructed attenuation coefficients $\mu(r,E)$ with an overlay for global spectral CT at monochromatic E=40, 70, 100 keV for 500 iterations, according to one embodiment.

FIG. 13A depicts a true color CT image reconstructed using the iterative framelet method, according to one implementation.

FIG. 13B depicts a true color CT image reconstructed using the SVD-based method, according to one implementation.

FIG. 14A depicts a true color CT image reconstructed using the iterative framelet method, according to one implementation.

FIG. 14B depicts a true color CT image reconstructed using the SVD-based method, according to one implementation.

DETAILED DESCRIPTION

The various embodiments disclosed and contemplated herein relate to imaging platforms and related systems, devices and methods that realize spectral CT by implementing algorithms on existing CT hardware platforms. Certain embodiments relate to machine vision systems having an imaging device with inconsistent lighting compensation. In exemplary embodiments of the system, a computer platform comprising a computer-readable media and a data processing system are provided for recording, monitoring and modifying the raw data and generating the visual images described herein.

It is understood that photons may be absorbed or scattered as the result of interaction with a material, such as during a scan. The most important process at low photon energy is the photoelectric effect (designated by $\phi$), which is the absorption of a photon with subsequent ejection of an atomic electron. The absorption coefficient for this photoelectric effect decreases as the photon energy increases. Scattering of photons by atomic electrons then takes a large contribution to the total attenuation coefficient (designated by $\mu$) in the middle energy range (for example 500 KeV to 5 MeV). In these settings, most scattering is Compton scattering (designated by $\theta$). Beyond 5 MeV the pair production effect dominates, in which a photon may be absorbed and produces a pair of an electron and a positron. Because the CT scanning implementations described here are focused on low- and middle-energy X-ray ranges, only photoelectric absorption and Compton scattering are considered, as it is possible to reconstruct the CT scan from these values for each given point r. Further explanation of the various implementations are found herein. It is understood that the disclosed implementations of the system can be performed in conjunction with the various techniques disclosed or otherwise described in Y. Wang, G. Wang, S. Mao, W. Cong, Z. Ji, J.-F. Cai, and Y. Ye, A Spectral Interior CT by a Framelet-Based Reconstruction Algorithm, Journal of X-Ray Science and Technology, 24(6): 771-785, 2016 and Y. Wang, G. Wang, S. Mao, W. Cong, Z. Ji, J.-F. Cai, and Y. Ye, A framelet-based iterative maximum-likelihood reconstruction algorithm for spectral CT, Inverse Problems, 32(11):115021(16pp), 2016, both of which are hereby incorporated by reference in their entirety.

Figure 1:
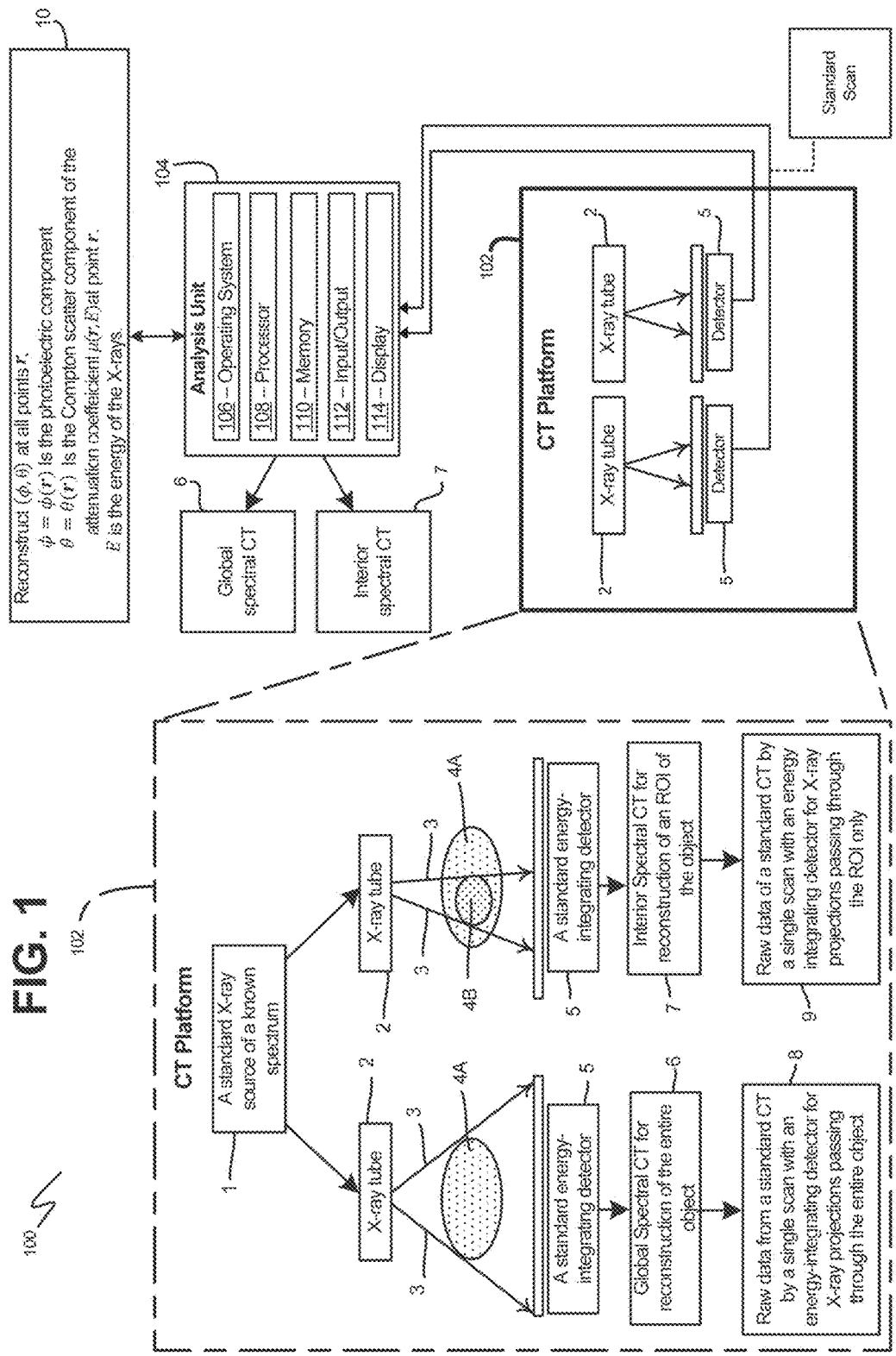
FIG. 1 is a schematic view of an exemplary embodiment of the disclosed system.

Turning to the figures in greater detail, the CT system 100 as shown in FIG. 1 has a typical CT platform 102 is shown and an analysis unit 104. In the implementation of FIG. 1, the analysis unit 104 can have an operating system 106, processor 108, memory 110, an input/output interface 112, display 114 and the like, as would be appreciated by one of skill in the art. The disclosed implementations can include an iterative spectral CT reconstruction algorithm assuming only one standard X-ray scan from the CT platform, such that the analysis unit 104 can be utilized to produce the reconstructed image as described herein, and as shown in box 10.

For example, in various embodiments, and as shown in FIG. 1, an X-ray scan of a known spectrum (box 1) is generated by an X-Ray tube (box 2) passing X-rays 3 through an object 4A or an internal region of interest ("ROI") 4B and receiving the X-rays 3 with a standard energy-integrating detector (box 5), as would be apparent to a skilled artisan. In various implementations, and as discussed herein, the global spectral CT (box 6) and interior spectral CT (box 7) are then reconstructed using the raw data from a single scan (boxes 8 and 9, respectively) using the disclosed system 100.

As would be appreciated by one of skill in the art, the reconstruction system 100 invokes a "non-linear inverse problem." As used herein, an "inverse problem" can be understood to mean a process for reconstructing a model (designated m) from observed data d. In these implementations, a "linear inverse problem" can be described by the linear equations d=Gm where G is a matrix multiplied to m. A "non-linear inverse problem," however, cannot be similarly formulated as a linear equation and is therefore inherently more difficult to solve.

As discussed herein in detail, the disclosed system 100 can implement an iterative algorithm using a polychromatic acquisition model with framelet sparsity. As is shown in the drawings and accompanying description, the various implementations of the disclosed CT system 100 are able to utilize a single standard X-ray scan by way of a data acquisition model, a framelet-based image processing method, and the presently disclosed algorithm. Experimental results are demonstrated in the accompanying examples and conclusions are also given herein.

Figure 2:
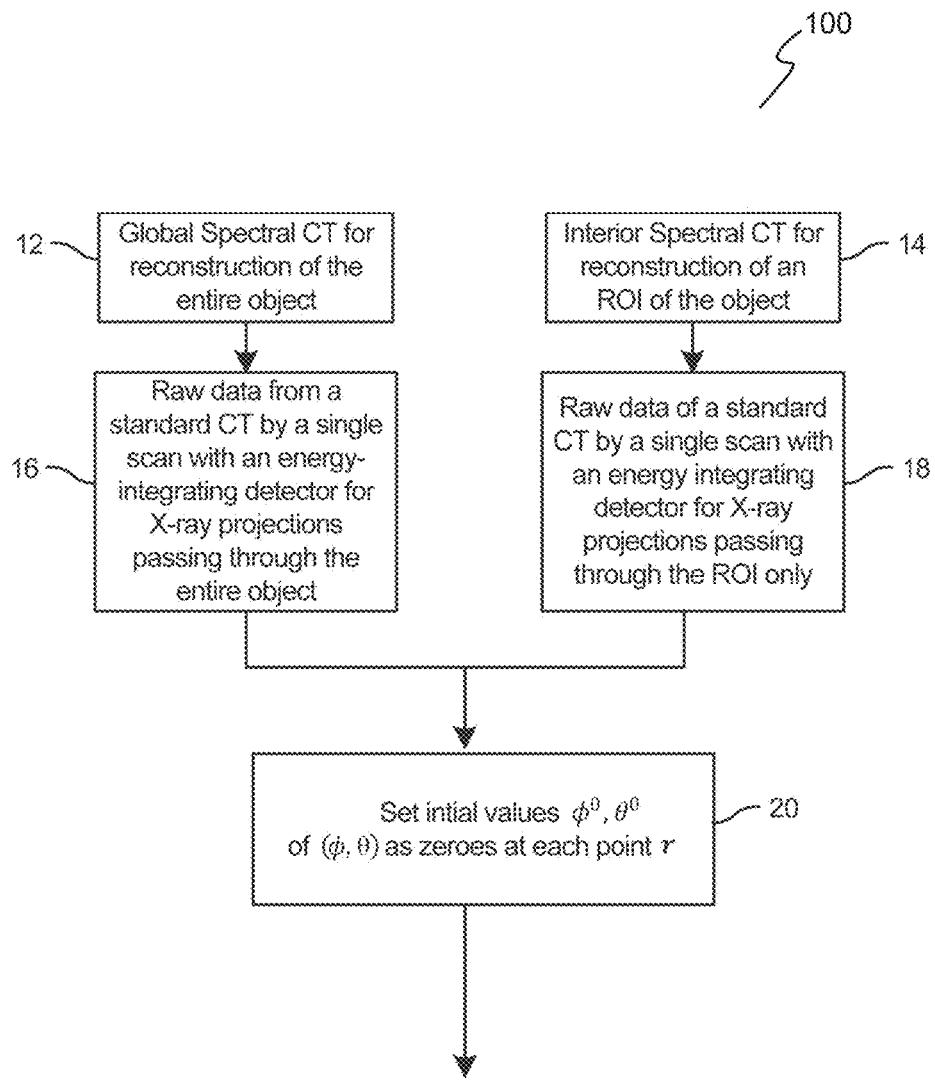
FIG. 2 is a flow chart depicting an exemplary implementation of the system, according to one embodiment.

As best shown in FIG. 2, exemplary implementations of the system 100 allow a user to initiate the reconstruction of the photoelectric component and Compton scatter component ($\phi$, $\theta$) at all points r in the entire object or ROI (shown at 4A and 4B in FIG. 1, respectively). In these implementations, $\phi=\phi(r)$ is the photoelectric component, $\theta=\theta(r)$ is the Compton scatter component of the attenuation coefficient $\mu(r,E)$ at point r, and E is the energy of the X-rays. In various implementations, a global spectral CT can be used for reconstruction of an entire object (box 12), or an interior spectral CT can be used for reconstruction of a ROI (box 14). In these implementations, raw data from a standard CT utilizing a single scan with an energy-integrating detector for X-ray projections can be utilized. For global spectral implementations, the scan is passed through the entire object (box 16), while in ROI implementations the scan is only passed through the ROI (box 18).

Continuing with FIG. 2, and as discussed further in relation to FIGS. 5-12, in exemplary implementations the disclosed system 100 assumes or assigns zero as the initial values $\phi^0, \theta^0$ of ($\phi$, $\theta$) at each point r (box 20). Skilled artisans will appreciate that a smooth function becomes larger along the direction of its gradient. A scaled gradient descent algorithm can be applied in the direction of the negative gradient of the objective function to minimize a negative maximum-likelihood function.

In certain of the forgoing examples, $\phi(r)$ and $\theta(r)$ can be discretized at all points r to $\phi_j$ and $\theta_j$, where j=1, . . . , J as a point index runs through all points r after the discretization. In these examples, $\phi=(\phi_1, \ldots, \phi_j)$ and $\theta=(\theta_1, \ldots, \theta_j)$ can be written as vectors. In one such example, $\phi_j^0$ and $\theta_j^0$, or $\phi^0=(\phi_1^0, \ldots, \phi_j^0)$ and $\theta^0=(\theta_1^0, \ldots, \theta_j^0)$ can be denoted, and the initial values selected as described above.

In certain of the forgoing examples, because the attenuation coefficients of the body can be approximated as piecewise constant or piecewise linear or piecewise smooth, it is possible to add a framelet sparse representation as a regularization term to the objective function, such that the final objective function is formulated as:

$$\min_{\phi,\theta} F(\phi, \theta) = \min_{\phi,\theta}(\lambda_1 \|W\phi\|_1 + \lambda_2 \|W\theta\|_1 - L) \quad (A)$$

where $\phi$ and $\theta$ are vectors of $\phi_j$ and $\theta_j$, j=1,2, . . . J respectively.

For the "smooth part" (−L), it is possible to use a scaled gradient descent method, while for the nonsmooth part, it is possible to utilize a soft-thresholding method defined by $$T_\lambda(x) = \frac{|x| - \lambda}{|x|} x$$

for $|x| > \lambda$, and zero elsewhere for the three-step iterative reconstruction algorithm as follows: (1) Set initial values $\phi_j^0$, $\theta_j^0$, (2) Iterate on n (3) The outcome of (2) $\phi^*_j$, $\theta^*_j$ is the solution of Eq. (A), which represents the attenuation coefficients at the reference energy $E_0$. And then the energy-dependent attenuation coefficients $\mu_{j,k}$ at any energy can be computed by solving for $\mu_{jk}$. In various implementations, these steps can be performed in any order.

Figure 3:
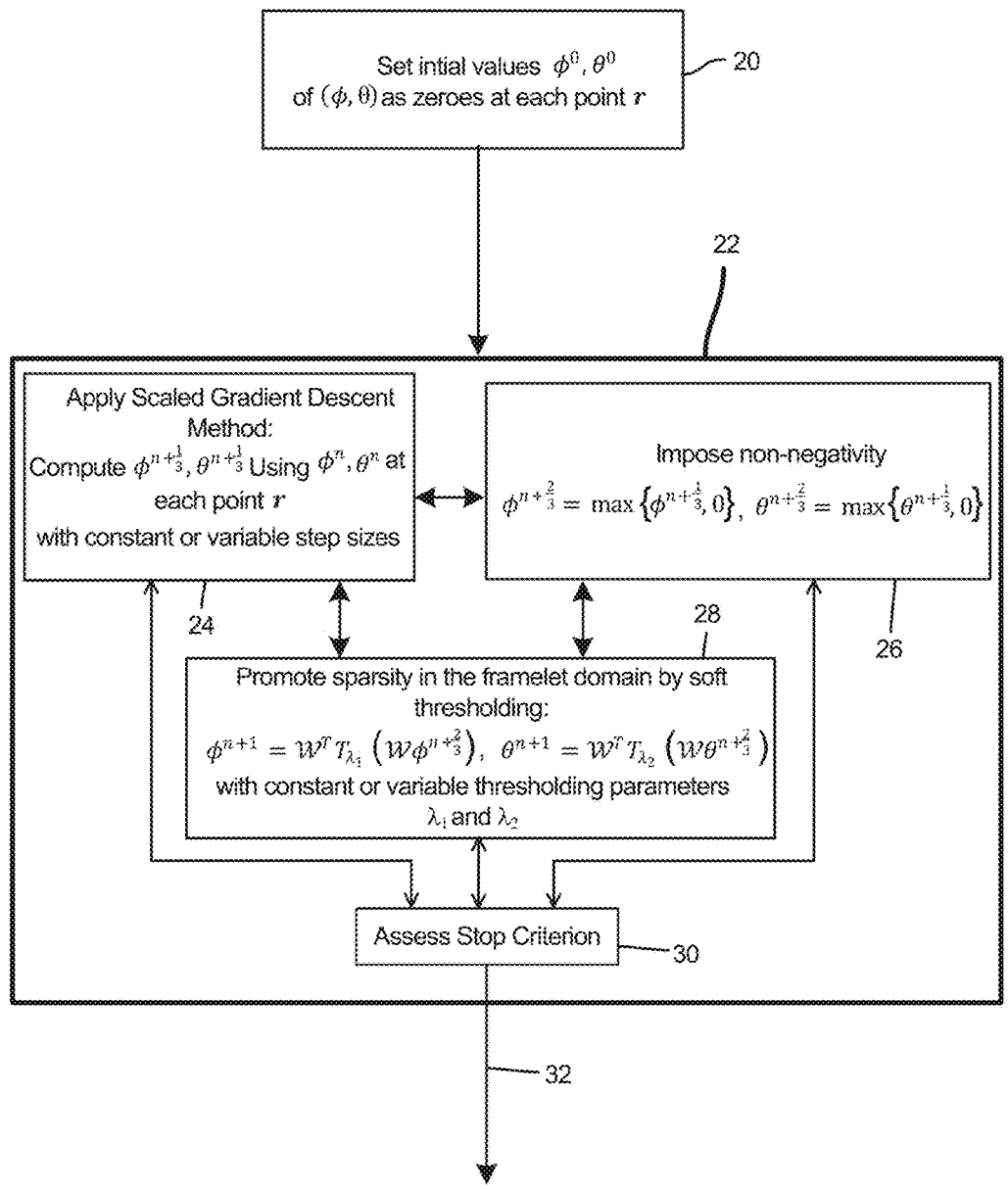
FIG. 3 is schematic overview of an implementation of the disclosed system executing the algorithm, according to one embodiment.

In one implementation, under an iteration algorithm, the superscript 0 can be used for $\phi$, $\theta$, $\phi_j$ and $\theta_j$ such that these will increase to positive fractions or integers. Turning to FIG. 3, after the initial values for $\phi^0$ and $\theta^0$ have been established (shown at box 20 in FIGS. 2-3—such as by an initial guess, described below), the system is configured to use the control unit 104 programmed to perform an iterative algorithm (box 22), which in this implementation is a framelet-based iterative maximum-likelihood reconstruction algorithm that iterates on n as follows:

$$\phi_j^{n+\frac{1}{3}} = \phi_j^n - \delta_1 \frac{\partial L}{\partial \phi_j}(\phi^n, \theta^n) \left( \sum_{h=1}^{J} \left( \frac{\partial^2 L}{\partial \phi_j \partial \phi_h} + \frac{\partial^2 L}{\partial \phi_j \partial \theta_h} \right)(\phi^n, \theta^n) \right)^{-1}$$

$$\phi_j^{n+\frac{2}{3}} = \max\left\{\phi_j^{n+\frac{1}{3}}, 0\right\}$$

$$\theta_j^{n+\frac{1}{3}} = \theta_j^n - \delta_2 \frac{\partial L}{\partial \theta_j}(\phi^n, \theta^n) \left( \sum_{h=1}^{J} \left( \frac{\partial^2 L}{\partial \theta_j \partial \phi_h} + \frac{\partial^2 L}{\partial \theta_j \partial \theta_h} \right)(\phi^n, \theta^n) \right)^{-1}$$

$$\theta_j^{n+\frac{2}{3}} = \max\left\{\theta_j^{n+\frac{1}{3}}, 0\right\}$$

$$\phi_j^{n+1} = \mathcal{W}^T T_{\lambda_1}\left(\mathcal{W} \phi_j^{n+\frac{2}{3}}\right)$$

$$\theta_j^{n+1} = \mathcal{W}^T T_{\lambda_2}\left(\mathcal{W} \theta_j^{n+\frac{2}{3}}\right)$$

where $L=L(\phi,\theta)$ is a log likelihood as defined herein in relation to Eqs. (7)-(10) and its formula is given in Eq. (10A). The operations in the last two equations above are given in Eq. (17) below. As is demonstrated herein, W is understood by those of skill in the art to be an operator which transfers $$\phi_j^{n+\frac{2}{3}} \text{ and } \theta_j^{n+\frac{2}{3}}$$

to the framelet domain, $T_{\lambda_1}$ and $T_{\lambda_2}$ are certain soft-thresholding operators, $\mathcal{W}^T$ is the operator which transfers the sparsified coefficients back to the ($\phi,\theta$) domain, and optionally, a stop criterion comprising a fixed number of iterations or stability of the resulting vectors $\phi^n$ and $\theta^n$ can be used.

Here $\delta_1$ and $\delta_2$ are step sizes for the $\phi$ and $\theta$ components, respectively. These step sizes may be taken as constant or variant coefficients and are allowed to change at each iteration step. They may have different values for different index j.

As described herein in greater detail, each iteration of exemplary implementations comprises three sub-steps which may be performed in any order. These sub-steps include: a rescaled gradient descent method (box 24); a non-negativity step (box 26), and a a thresholding operation (box 28), as are described herein. It will be appreciated by those of skill in the art that various additional steps may be performed, and that certain of these steps may be performed in any order and any number of times until the stop criterion (box 30) are reached.

In one sub-step, the system can apply a rescaled gradient descent method (box 24) to decrease the $l_2$-norm error in fitting the polychromatic acquisition model. Further discussion of this step can be found in relation to Eqs. (14) and (15), below.

In another sub-step, non-negativity is imposed (box 26), such that negative components are set to 0 to keep positivity of the attenuation coefficients ($\phi,\theta$). In implementations of this step, if any of computed values $$\phi^{n+\frac{1}{3}}, \theta^{n+\frac{1}{3}}$$

are negative, it is possible to reset that negative value to zero at each point r to promote processing. Further discussion of this step can be found in relation to Eq. (16), below.

In another sub-step, a thresholding operation (box 28) is performed on framelet coefficients to make the image sparse in the framelet domain. A tight frame system is a generalization of an orthonormal basis of a Hilbert space and can be overcomplete and redundant. As would be appreciated by a skilled artisan, a framelet system is a tight frame system which has a wavelet structure. In various implementations, the framelet system can utilize discrete framelets, such as those previously constructed by Daubechies. Further discussion of this step can be found in relation to Eq. (17), below.

For example, the method of soft thresholding can include the discrete framelet system described above, wherein one transforms $$\phi^{n+\frac{2}{3}}, \theta^{n+\frac{2}{3}}$$

to the framelet domain, i.e., expresses $$\phi^{n+\frac{2}{3}}, \theta^{n+\frac{2}{3}}$$

as linear combinations of the framelets. In this example, small coefficients can be set to zero by soft thresholding, and the algorithm can then transform the sparsified coefficients back to φ, θ and name them $\phi^{n+1}$, $\theta^{n+1}$. This step represents a denoising procedure using framelet sparsity.

In the disclosed implementations, the various sub-steps can be performed in any order within an iterative cycle. In any event, the present system 100 can also apply a standard iteration stop criterion (box 30) such as the mean square error ("MSE") criterion or the successive difference criterion. If this stop criterion is not met, the iterations (box 22) continue until the criterion has been met. When the stop criterion is satisfied, the system is able to terminate the iteration and output the outcome: $\phi=\phi^{n+1}$, $\theta=\theta^{n+1}$ at each point r (arrow 32 in FIG. 3 to box 34 in FIG. 4).

Figure 4:
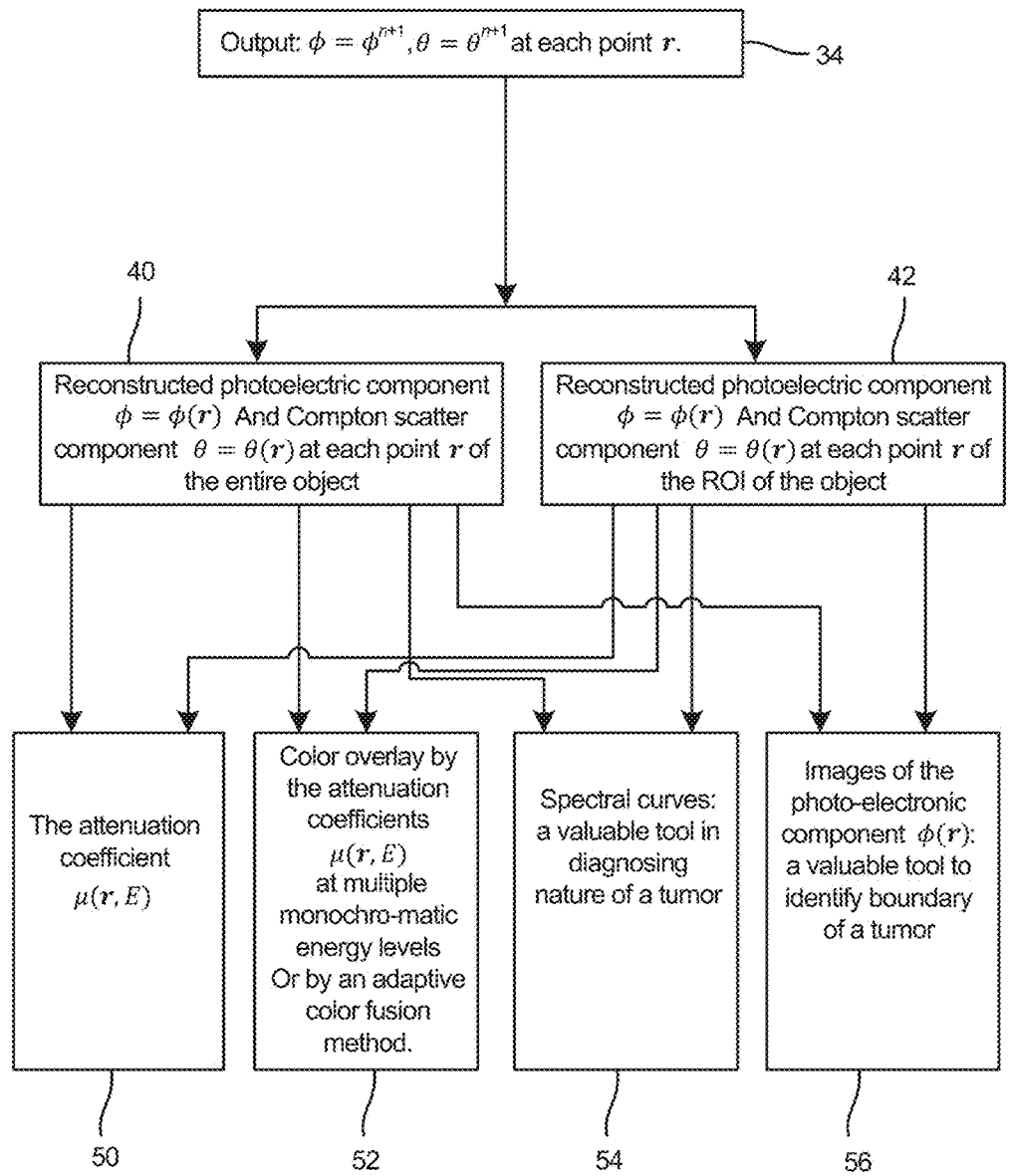
FIG. 4 further schematic view of an implementation of the disclosed system, according to one embodiment.

As shown in FIG. 4, the photoelectric component φ=φ(r) and Compton scatter component θ=θ(r) at each point r can then be reconstructed for either the entire object (box 40) or the ROI (box 42).

In various implementations, as shown in box 50, the attenuation coefficient μ(r,E) can be established (box 50). Further discussion can be found in relation to Eq. (1) and (2).

In various implementations, as shown in box 52, a color overlay may be performed by the attenuation coefficients μ(r,E) at multiple monochromatic energy levels, or by an adaptive color fusion method, as is discussed below. Further discussion can be found in relation to FIGS. 9C and 9D.

In various implementations, as shown in box 54, spectral curves can be generated. These spectral curves can provide a valuable tool in diagnosing nature of a tumor. Further discussion can be found in relation to FIG. 10.

In various implementations, as shown in box 56, images of the photo-electronic component φ(r) can also be generated, which can provide a valuable tool to identify boundary of a tumor. Further discussion can be found, for example, below and in relation to FIGS. 9A-9D. A further discussion of various aspects of the presently disclosed system and algorithms follows.

I. POLYCHROMATIC ACQUISITION MODEL AND ITERATIVE ALGORITHM

A. Attenuation Coefficient, Reconstruction and Data Acquisition Model

Figure 5:
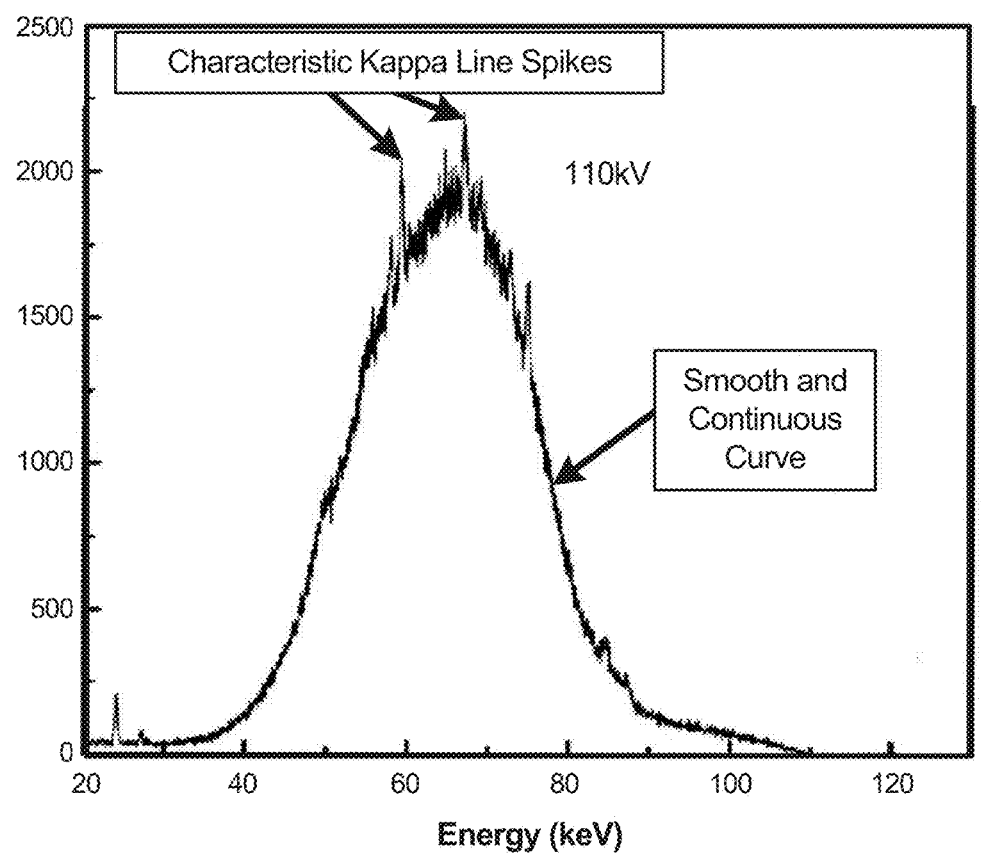
FIG. 5 depicts a model spectral curve $I_0(E)$ of an X-ray tube, according to one implementation.

A polychromatic acquisition model is incorporated into the algorithm used in various implementations. FIG. 5 depicts a spectral curve $I_0(E)$ of an X-ray tube. As shown in the spectral curve of FIG. 5, in most portions of the curve, a smooth and continuous curve can be observed due to the effect of bremsstrahlung. In other portions, characteristic ϰ (kappa) line spikes for certain atoms can be seen, as is also depicted in FIG. 5.

The X-ray attenuation coefficient is given by μ(r,E) at the point r∈Ω for the energy E of the X-ray, where Ω is the image domain. Accordingly, the attenuation coefficient can be approximated as follows:

$$\mu(r,E)=\phi(r)\Phi(E)+\theta(r)\Theta(E) \quad (1)$$

Where the photoelectric component is φ(r) and the Compton scatter component is θ(r), both being independent of the energy E. Further, Θ(E) is defined by the Klein-Nishina function, as follows:

$$\Theta(E) = \frac{1+\varepsilon}{\varepsilon^2}\left(\frac{2(1+\varepsilon)}{1+2\varepsilon} - \frac{1}{\varepsilon}\log(1+2\varepsilon)\right) + \frac{1}{2\varepsilon}\log(1+2\varepsilon) - \frac{1+3\varepsilon}{(1+2\varepsilon)^2} \quad (2)$$

where ε=E/511 keV.

In this implementation, L represents a straight line passing through an object Ω which presents an X-ray beam. The initial intensity of beam L can be denoted by $I_0(E)$, with photon energy E. Accordingly, the intensity measured by the detector of the beam L is as follows:

$$I = \int_0^\infty I_0(E)\exp\left(-\int_L \mu(r,E)dr\right)dE. \quad (3)$$

From Eq. (3), it is possible to reconstruct the attenuation coefficient μ from I. As such, this no longer presents a linear problem because a logarithmic transfer is non-linear. When the X-ray source is a monoenergectic source, μ(r,E)=μ(r), and $I_0(E)=I_0$. Therefore (3) can be expressed as:

$$I=I_0 \exp(-\int_L \mu(r)dr) \quad (4)$$

It is thereafter possible to reconstruct the attenuation coefficients μ(r) after taking the logarithm on each side of Eq. (4).

Under standard theory, the reconstruction problem can be made linear by the mean value theorem of integrals. Accordingly, Eq. (3) can be reduced to:

$$I = \exp\left(-\int_L \mu(r,\overline{E})dr\right)\int_0^\infty I_0(E)dE \quad (5)$$

where $\overline{E}$ is the equivalent energy.

From Eq. (5), if I is denoted as $I(\overline{E})$ and $\int_0^\infty I_0(E)dE$ as $I_0(\overline{E})$, the result is given by:

$$\int_L \mu(r,\overline{E})dr = \log\left(\frac{I_0(\overline{E})}{I(\overline{E})}\right) \quad (6)$$

Because the $\log(I_0(\overline{E})/I(\overline{E}))$ term can be computed from the scanning data, the $\int_L \mu(r,E)dr$ term is known for all X-ray beams L passing through Ω.

Using Eq. (6), the reconstruction of μ(r,$\overline{E}$) for r∈Ω becomes a linear problem which can be solved by conventional methods. However, the reconstructed linear attenuation coefficients μ(r,$\overline{E}$) given by Eq. (6) are actually the linear coefficients at an equivalent energy $\overline{E}$, which is regarded as independent of the energy E and therefore do not provide spectral information. Accordingly, the approximation μ(r,E)=μ(r,$\overline{E}$), produces beam-hardening artifacts, because equivalent energy $\overline{E}$ is increased: the lower energy spectrum will be absorbed in higher proportions than the higher energy spectrum. In order to address these artifacts, the presently disclosed CT system 100 utilizes an iterative reconstruction algorithm for spectral CT.

As has been previously described in a discrete setting, photon energy E can be discretized as $E_k$, k=1, 2, ..., K, the measurements discretized as $y_i$, i=1, 2, ..., M, and the linear attenuation coefficients discretized as $\mu_{jk}$ for j=1, 2, ..., J, and k=1, 2, ..., K. Here i,j,k are the indices of measurements, image pixels, and energy levels, respectively, and M,J,K are total numbers of measurements, image pixels and energy levels. Thus, in a discrete setting the model value for $\hat{y}_i$ should be given by:

$$\hat{y}_i = \sum_{k=1}^{K} b_{ik} \exp\left(-\sum_{j=1}^{J} l_{ij}\mu_{jk}\right) \quad (7A)$$

where $b_{ik}$ is the total intensity detected by detector i without the scanned object for incident photons of energy $E_k$, given by:

$$b_{ik} = I_{ik} S_k E_k \quad (7B)$$

Where $I_{ik}$ is the incident number of photons, $S_k$ is the detector sensitivity factor, and $E_k$ is photon energy (keV). The factor $E_k$ is introduced because the detectors of CT (most CT machines use scintillation-type detectors) are energy-counting, while in nuclear medicine they use photon-counting detectors. The measurement $y_i$ approximately follows a Poisson distribution with an expectation $\hat{y}_i$, where the probability density function is:

$$p(y_i) = \frac{\hat{y}_i^{y_i} \exp(-\hat{y}_i)}{y_i!} \quad (7C)$$

Given that for any given i, $y_i$ is an independent Poisson random variable with expectation $\hat{y}_i$, the log-likelihood is given by:

$$\sum_{i=1}^{M} (y_i \log \hat{y}_i - \hat{y}_i). \quad (8)$$

The number of unknowns in (7A) is JK. Vector space can be introduced to reduce the total of unknowns. That is, the energy-dependent linear attenuation coefficients $\mu_{jk}$ can be linearly represented by basis functions. Further, the energy-dependent attenuation coefficient(s) ($\mu_{jk}$) can be decomposed into two base functions from the photoelectric component and the Compton scatter component, as follows:

$$\mu_{jk} = \phi_j \Phi(E_k) + \theta_j \Theta(E_k) \quad (9)$$

Eq. (9) therefore represents the discrete version of Eq. (1), where:

$$\Phi(E_k) = \frac{\frac{1}{E_k^3}}{\frac{1}{E_0^3}} = \frac{E_0^3}{E_k^3},$$

where $E_0$ is a reference energy (e.g., $E_0$=70 keV), and $$\Theta(E_k) = \frac{\Theta(E_k)}{\Theta(E_0)}$$

with $\Theta$ in Eq. (2). Here $\phi_j$ represents the photoelectric component at energy $E_0$, and $\theta_j$ represents the Compton scatter component at $E_0$.

Having performed this decomposition, the number of unknowns is then 2J, a significant reduction from that given by Eq. (7A). To further reduce the number of unknowns to J, a least squares fit is applied to $\phi_j$ and $\theta_j$, j=1, 2, ..., J, obtaining an analytic expression of $\phi_j$ and $\Theta_j$ in terms of $\mu_j$.

In various implementations of the presently disclosed system 100 and associated algorithms, no reduction in the number of the 2J unknowns is performed to maintain the spectral information. Instead, the $\mu_{jk}$ term is substituted in Eq. (7A) with that of Eq. (9) to give the present acquisition model:

$$\hat{y}_i = \sum_{k=1}^{K} b_{ik} \exp\left(-\sum_{j=1}^{J} l_{ij}(\phi_j \Phi(E_k) + \theta_j \Theta(E_k))\right) \quad (10)$$

Further substituting Eq. (10) into Eq. (8), a log-likelihood $L(\phi,\theta)$ is given, where $\phi$ and $\theta$ represent column vectors of $\phi_j$ and $\theta_j$ for j=1, 2, ..., J, respectively as follows:

$$L(\phi, \theta) = \sum_{i=1}^{M} \left( y_i \log\left[\sum_{k=1}^{K} b_{ik} \exp\left(-\sum_{j=1}^{J} l_{ij}(\phi_j \Phi(E_k) + \theta_j \Theta(E_k))\right)\right] - \left[\sum_{k=1}^{K} b_{ik} \exp\left(-\sum_{j=1}^{J} l_{ij}(\phi_j \Phi(E_k) + \theta_j \Theta(E_k))\right)\right]\right) \quad (10A)$$

B. Tight Frame and Framelet System

Tight frame and framelet applications are used to establish the algorithm utilized in the presently disclosed systems, methods and devices for sparse representation of the energy-dependent attenuation coefficients.

In the present examples, $\mathcal{H}$ represents a Hilbert space. In these examples, a countable set $\mathcal{F} \subset \mathcal{H}$ can be referred to as a "frame" if the analysis operator is bounded above and below, such as:

$$C_2 \|f\|^2 \leq \sum_{g \in \mathcal{F}} |\langle f, g\rangle|^2 \leq C_1 \|f\|^2, \forall f \in \mathcal{H}$$

where $\langle \bullet, \bullet \rangle$ is the inner product and $\|\bullet\|$ is the norm in the Hilbert space.

Accordingly, if $C_1 = C_2$, the system $\mathcal{F}$ is called a "tight frame". It can be assumed that $C_1 = C_2 = 1$ in tight frames, thereby giving:

$$\|f\|^2 = \sum_{g \in \mathcal{F}} |\langle f, g\rangle|^2, \forall f \in \mathcal{H} \quad (11)$$

which is equivalent to:

$$f = \sum_{g \in \mathcal{K}} \langle f, g\rangle g, \forall f \in \mathcal{H} \quad (12)$$

As would be apparent to a skilled artisan, orthonormal basis is a tight frame, because the conditions of Eqs. (11) and (12) hold for any orthonormal bases in $\mathcal{H}$. However, it is understood that a tight frame is not necessarily an orthonormal basis. Accordingly, the analysis operator (or decomposition operator) D: $\mathcal{H} \to l_2(\mathbb{Z})$ can be defined by:

$$Df = \{<f,g>\}_{g \in \mathcal{F}}, \text{ for any } f \in \mathcal{H},$$

and the synthesis operator R:$l_2(\mathbb{Z}) \to \mathcal{H}$ is defined by:

$$Rw = \sum_{g \in \mathcal{F}} w_g g,$$

for any $$w = \{w_g\}_{g \in \mathcal{F}} \in l_2(\mathbb{Z}).$$

It is therefore clear that R=D*, and condition (12) implies: DD*=I.

However, typically DD* ≠I. Therefore, tight frame can serve as a generalization of orthonormal basis. A tight frame system can also be overcomplete and redundant. The advantage of tight frame system over orthonormal basis for image representation as is discussed further in Jian-Feng Cai, Raymond H. Chan, Zuowei Shen, A framelet-based image in painting algorithm, Applied and Computational Harmonic Analysis, Volume 24, Issue 2, 2008, Pages 131-149, which is incorporated herein by reference.

There are many tight frame systems that can sparsely represent piecewise smooth functions, including framelets and curvelets. The present implementations use framelets to sparsely represent the photoelectronic component and Compton scatter component of the attenuation coefficients.

Framelet systems are tight frames having a wavelet structure and constructed from the unitary extension principle ("UEP"). The present implementations focus on the description of discrete framelet transformations, as numerical computations are eventually performed in the discrete form. Each framelet system is associated with a family of discrete sequences $\{h_i\}_{i=0}^s$, called filters. Among them, $h_0$ is referred to as the "low-pass filter," and the others are "high-pass filters." The one level non-downsampling discrete framelet transform is given by:

$$D = \begin{bmatrix} h_0 * \\ \vdots \\ h_S * \end{bmatrix} \quad (13)$$

where $h_i*$, i=0, 1, . . . s, is the matrix form of the discrete convolution with kernel $h_i$. To establish a multi-level decomposition, we just need to apply the matrix D in (13) to $h_0*$ recursively. When the filters satisfies UEP, the rows of D will form a tight frame in the Euclidean space, i.e. DD*=I.

A family of framelet systems can be constructed from the B-splines with different orders. In the univariate case, the piecewise constant B-spline framelet system (known as the Haar wavelet system) is given by:

$$h_0 = \frac{1}{2}[1, 1], h_1 = \frac{1}{2}[1, -1]$$

Filters of the framelet from piecewise linear B-spline are accordingly given by:

$$h_0 = \frac{1}{4}[1, 2, 1], h_1 = \frac{\sqrt{2}}{4}[1, 0, -1], h_2 = \frac{1}{4}[-1, 2, -1]$$

The presently-disclosed attenuation coefficients have two spatial directions. Therefore, bivariate framelet system will be used in the present examples. These filters are obtained by tensor products of the corresponding univariate filters. In particular, the filters in bivariate Haar wavelet system are given by:

$$h_0 = \frac{1}{4}\begin{bmatrix} 1 & 1 \\ 1 & 1 \end{bmatrix},$$

$$h_1 = \frac{1}{4}\begin{bmatrix} 1 & -1 \\ 1 & -1 \end{bmatrix},$$

$$h_2 = \frac{1}{4}\begin{bmatrix} 1 & 1 \\ -1 & -1 \end{bmatrix},$$

$$h_3 = \frac{1}{4}\begin{bmatrix} 1 & -1 \\ -1 & 1 \end{bmatrix}$$

This framelet system is used in the present examples. Filters for higher-order bivariate framelet systems can also be constructed in a similar way.

C. The Framelet-Based Iterative Algorithm

In the present examples and implementations, an iterative algorithm for the reconstruction of the energy-dependent attenuation coefficients μ(r,E) is given. Further, in various implementations, a framelet-based model is used to approximate μ(r,E). Therefore, only the photoelectronic component ϕ and Compton scatter component θ are required to reconstruct the general image or ROI, as is discussed in relation to FIGS. 2-4. Because the linear attenuation coefficients of human body are usually approximately as being piecewise smooth, the present implementations assume that both ϕ and θ are approximately piecewise smooth as well. Further, and as is also discussed in relation to FIGS. 2-4, the non-negativity of ϕ and θ are enforced in certain steps.

In various implementations, the coefficients ϕ and θ should satisfy certain constraints. First, the coefficients should fit the polychromatic data acquisition model of Eq. (7A) with Poisson noise. Further, the coefficients should be nonnegative, as is discussed above. Finally, they should be sparse in the framelet domain. The implementations of the disclosed iterative algorithm force the iterates to satisfy these constraints alternatively, as disclosed herein.

1. The Rescaled Gradient Descent Method

Returning to the sub-steps or steps outlined above in FIG. 3 in box 22, in certain implementations a scaled gradient descent method (box 24) is applied in certain implementations. In the discretized setting $\phi = (\phi_1, \ldots, \phi_J)$ and $\theta = (\theta_1, \ldots, \theta_J)$ in one application $\phi(r)$ and $\theta(r)$ can be discretized at all points r to $\phi_j$. In this Example, let $\phi^n = (\phi_1^n, \ldots, \phi_J^n)$ and $\theta^n = (\theta_1^n, \ldots, \theta_J^n)$ be the current iterates. Let $\phi^n$ and $\theta^n$ be the current iterates. To fit the model given by Eq. (7A) with Poisson noise, it is important to decrease 'L(ϕ,θ) in Eqs. (8) and (10), as is described further above. It is possible to use a scaled gradient descent to minimize −L(ϕ,θ). Accordingly, various implementations employ a step of scaled gradient descent to decrease −L(ϕ,θ). This step therefore yields:

$$\phi_j^{n+\frac{1}{3}} = \phi_j^n + \delta_1 \Delta \phi_j^n, \theta_j^{n+\frac{1}{3}} = \theta_j^n + \delta_2 \Delta \theta_j^n \quad (14)$$

where $\delta_1$ and $\delta_2$ are step sizes for the $\phi$ and $\theta$ components as discussed above, and $$\Delta \phi_j^n = -\frac{\partial L}{\partial \phi_j}(\phi^n, \theta^n)\left(\sum_{h=1}^{J}\left(\frac{\partial^2 L}{\partial \phi_j \partial \phi_h} + \frac{\partial^2 L}{\partial \phi_j \partial \theta_h}\right)(\phi^n, \theta^n)\right)^{-1}, \quad (15)$$

$$\Delta \theta_j^n = -\frac{\partial L}{\partial \theta_j}(\phi^n, \theta^n)\left(\sum_{h=1}^{J}\left(\frac{\partial^2 L}{\partial \theta_j \partial \phi_h} + \frac{\partial^2 L}{\partial \theta_j \partial \theta_h}\right)(\phi^n, \theta^n)\right)^{-1}$$

2. Non-Negativity

Next, and as shown in FIG. 3, various implementations feature a non-negativity step (box 26). In these implementations, it is possible to project the $$\phi_j^{n+\frac{1}{3}} \text{ and } \theta_j^{n+\frac{1}{3}} \phi^{n+\frac{1}{3}} \text{ and } \theta^{n+\frac{1}{3}}$$

terms onto the non-negative cone, defined here as a region of vectors with all their components being non-negative, to enforce the non-negativity of the photoelectronic component and the Compton scatter component of the attenuation coefficients. For example:

$$\phi_j^{n+\frac{1}{3}} = \max\left\{\phi_j^{n+\frac{1}{3}}, 0\right\}, \theta_j^{n+\frac{2}{3}} = \max\left\{\theta_j^{n+\frac{1}{3}}, 0\right\} \quad (16)$$

3. Thresholding

Various implementations incorporate the sparsity promotion step (box 28). In these implementations, the system can promote the sparsity of $\phi=(\phi_1, \ldots, \phi_J)$ and $\theta=(\theta_1, \ldots, \theta_J)$ in the framelet domain as follows. These $\phi=(\phi_1, \ldots, \phi_J)$ and $\theta=(\theta_1, \ldots, \theta_J)$ are transformed into the framelet domain, where small coefficients are set to 0 by soft-thresholding, and the sparsified coefficients are correspondingly transformed back to $\phi=(\phi_1, \ldots, \phi_J)$ and $\theta=(\theta_1, \ldots, \theta_J)$. More precisely, these implementations define the terms as follows:

$$\phi^{n+1} = W^T T_{\lambda_1}\left(W\phi^{n+\frac{2}{3}}\right), \quad (17)$$

$$\theta^{n+1} = W^T T_{\lambda_2}\left(W\theta^{n+\frac{2}{3}}\right)$$

where $T_\lambda(\cdot)$ is the soft-thresholding operator defined by $$T_\lambda(x) = \frac{|x|-1}{|x|}x \text{ if } |x| > \lambda,$$

and zero otherwise. Here $\lambda_1$ and $\lambda_2$ are thresholding parameters which are allowed to change at each iteration step. The definitions of Eq. (17) can also act as a denoising procedure using framelet sparsity, and this approach minimizes an objective function involving a balanced sparsity of framelet coefficients. The steps of Eq. (14) through Eq. (17) are repeated alternatively until convergence, as described above in relation to FIGS. 2-4.

Accordingly, in exemplary implementations of the system, an algorithm is provided as described (1), such that the system sets initial values for $\phi^0=(\phi_1^0, \ldots, \phi_J^0)$ and $\theta^0=(\theta_1^0, \ldots, \theta_J^0)$ and (2) the proceeds to iterate on n as follows:

$$\phi_j^{n+\frac{1}{3}} = \phi_j^n - \delta_1 \frac{\partial L}{\partial \phi_j}(\phi^n, \theta^n)\left(\sum_{h=1}^{J}\left(\frac{\partial^2 L}{\partial \phi_j \partial \phi_h} + \frac{\partial^2 L}{\partial \phi_j \partial \theta_h}\right)(\phi^n, \theta^n)\right)^{-1}$$

$$\phi_j^{n+\frac{2}{3}} = \max\left\{\phi_j^{n+\frac{1}{3}}, 0\right\}$$

$$\theta_j^{n+\frac{1}{3}} = \theta_j^n - \delta_2 \frac{\partial L}{\partial \theta_j}(\phi^n, \theta^n)\left(\sum_{h=1}^{J}\left(\frac{\partial^2 L}{\partial \theta_j \partial \phi_h} + \frac{\partial^2 L}{\partial \theta_j \partial \theta_h}\right)(\phi^n, \theta^n)\right)^{-1}$$

$$\theta_j^{n+\frac{2}{3}} = \max\left\{\theta_j^{n+\frac{1}{3}}, 0\right\}$$

$$\phi_j^{n+1} = W^T T_{\lambda_1}\left(W\phi_j^{n+\frac{2}{3}}\right)$$

$$\theta_j^{n+1} = W^T T_{\lambda_2}\left(W\theta_j^{n+\frac{2}{3}}\right)$$

until the standard iteration stop criterion (shown at box 30 in FIG. 3) is reached and the CT image is reconstructed.

4. SVD-Based Color Fusion Method

In certain implementations, the system features an adaptive color fusion method based on the singular value decomposition ("SVD"). These implementations utilize principal component analysis ("PCA") to address spectral information for X-ray data and in order to choose the RGB components adaptively. Accordingly, a method was developed based on singular value decomposition using the correlation of images corresponding to different energies. These implementations allow the user to adaptively choose three images corresponding to the first three bigger eigenvalues as the RGB components.

Specifically, this SVD color fusion method is performed as follows:

In a first step, $\mu(r, E_K)$ is assigned at each energy $E_K$, k=1, 2, … K as a column vector $x_K$, and the matrix X is with each column $x_K$, $$X = x_1, x_2, \ldots x_K. \quad (18)$$

In a second step, singular value decomposition is performed on X, for example:

$$X = USV^T, \quad (19)$$

where the superscript T means taking transposition of a matrix.

In a third step, the first three bigger singular value in S is chosen, and the remaining singular values are set to 0 to get $X_{new}$, and then $$X_{new} = US_{new}V^T. \quad (20)$$

In a fourth step, the first three columns of $X_{new}$ are chosen as the RGB components in Eq. (21) to get a color image by Eq. (22), as described below.

In these implementations, in reconstructing $\mu(r,E)$ at any energy E, three images can be chosen corresponding to three different energies—such as 40, 70, 100 keV—as the RGB components. That is:

$$R=\mu(r,40),\ G=\mu(r,70),\ B=\mu(r,100), \quad (21)$$

and then linearly fit the RGB components to obtain the color image as $$\mu_{color}=a_1R+a_2G+a_3B, \quad (22)$$

As would be understood by one of skill in the art, various other reconstructions are possible. Accordingly, further implementations and energy choices are possible for implementations utilizing alternate display types for various two- and three-dimensional reconstruction types.

II. RESULTS

A. Example I: Synthesized Data

As best shown in FIGS. 6A-8C, a 2D Shepp-Logan phantom was used to assess the various implementations of the system. The Shepp-Logan phantom ("phantom") is a widely-used synthesized phantom for testing algorithms in CT, and is well understood in the art. There are several ellipses in the phantom. In the present simulations, a variety of substances were placed in the ellipses to generate presently-disclosed example phantom and the corresponding reconstructed images.

Figure 7A:
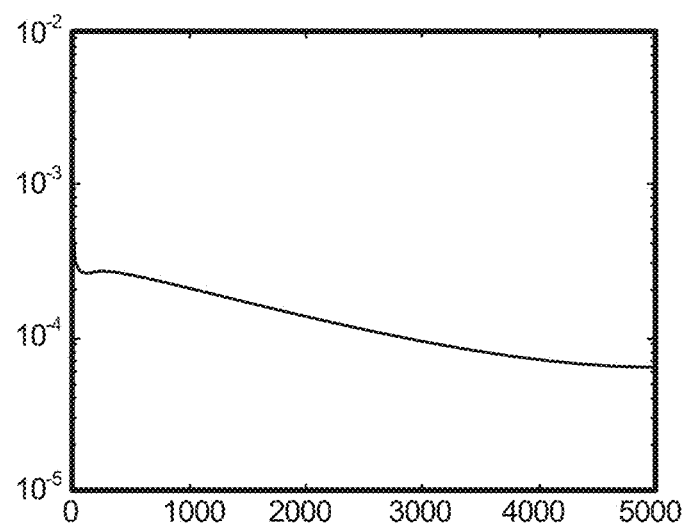
FIG. 7A depicts a chart of the mean square error against the number of iterations for the simulated $\phi$, according to one implementation.
Figure 7B:
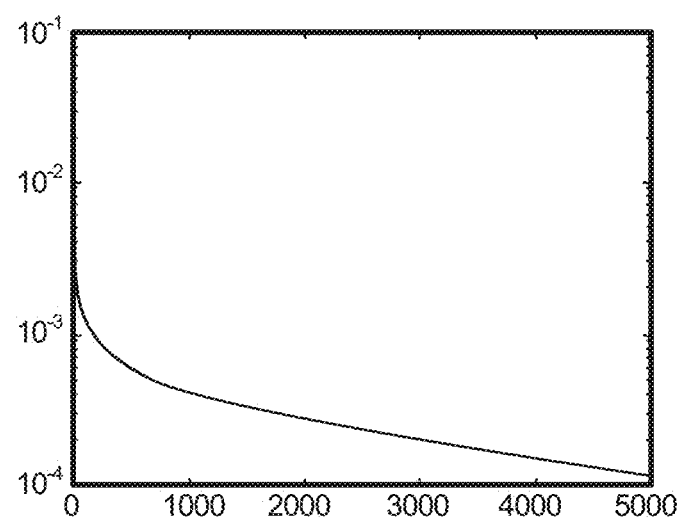
FIG. 7B depicts a chart of the mean square error against the number of iterations for the simulated $\theta$, according to one implementation.
Figure 8A:
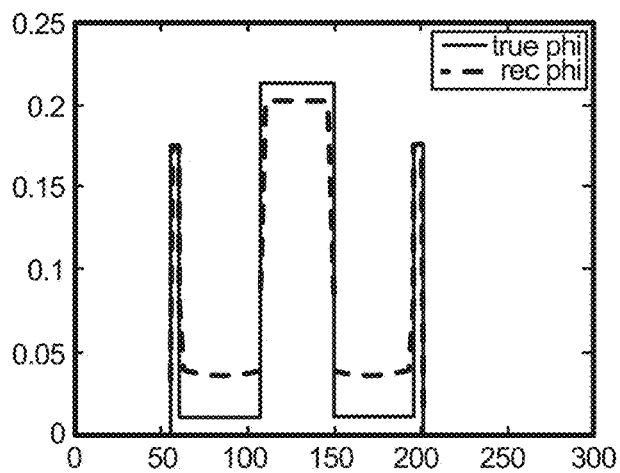
FIG. 8A depicts the profile of reconstructed photoelectric component, $\phi$, according to one implementation.
Figure 8B:
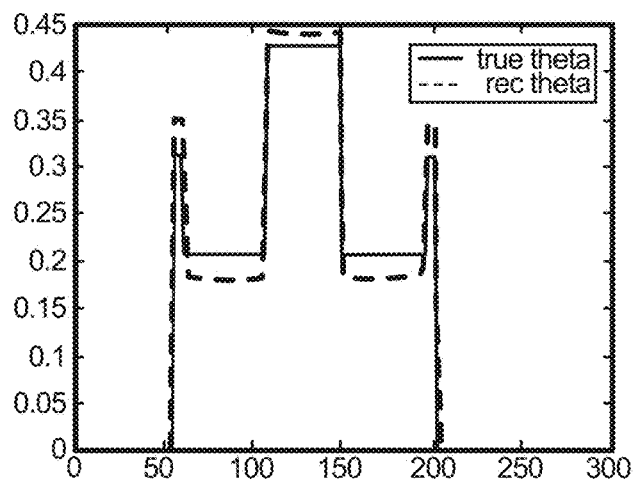
FIG. 8B depicts the profile of reconstructed Compton scatter component, $\theta$, according to one implementation.
Figure 8C:
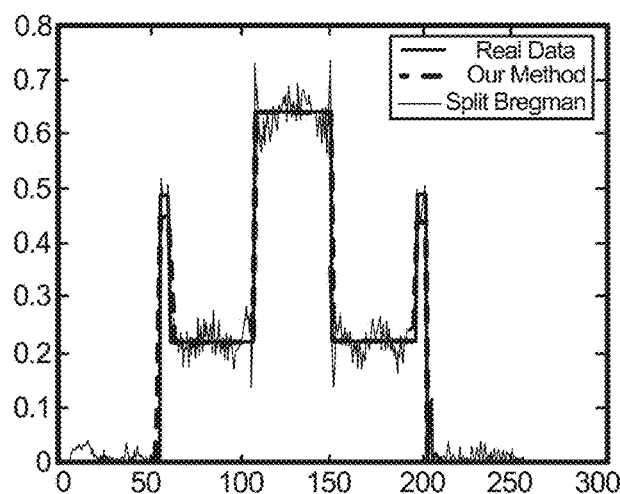
FIG. 8C depicts the profile of reconstructed attenuation coefficient $\mu$, according to one implementation.

FIGS. 6-8 are reconstructed images demonstrating one example showing that the disclosed algorithm can be applied to reconstruct less-dense substances, such as soft tissue, bone, and aluminum. The reconstructed images are shown in FIGS. 6A-8C. In these examples, a fan-beam imaging geometry was employed. In this example, the circular scanning locus is of radius 57 cm, and the diameter of the FOV is 22.4 cm corresponding to 672 detector bins, each element of which is 0.033 cm. The resolution of reconstructed images is 256×256, so that each pixel has a size of 0.078125 cm by 0.078125 cm. In these simulations, 30 projection views for a 360° scan were used for our test phantom. Namely, the system matrix had 672×30 rows and 256×256 columns. This system matrix is energy-independent and determined by the CT system, whose element is the length of the intersection between one X-ray and one pixel of the scanned object (corresponding to the $l_{ij}$ in Eq. (7A)). In this example, the X-ray spectrum is simulated by 25 discrete different energy in the range [20 140] keV. All simulated measurements are contaminated by Poisson noise with the mean in Eq. (7A). The presently-disclosed algorithm was used to reconstruct the photoelectric coefficients φ and Compton scatter coefficients θ. The step size $\delta_1=0.5$ for φ and $\delta_2=1$ for θ were used for the example phantom. The threshold parameters $\lambda_1$ and $\lambda_2$ are chosen empirically. In the present example, the iteration was stopped after 3000 steps, though other ranges can be used, as would be apparent to one of skill in the art.

In these studies, the most outer ellipsoidal shell is filled by bone, and majority part of the phantom by plexiglass; the two slant ellipses are air, and the remaining ellipses are made of aluminum. Table 1 compares the intensities of several substances placed in the Shepp-Logan phantom, which are used for generating the underlying photoelectric coefficients φ and Compton scatter coefficients θ.

TABLE 1

Simulated φ, θ and $\mu_{70\ keV}$ for Bone, Water, Air, Plexiglass, and Aluminum.

| Substance | φ(1/cm) | θ(1/cm) | $\mu_{70\ keV}$(1/cm) |
|---|---|---|---|
| Bone | 0.1757 | 0.3109 | 0.4974 |
| Water | 0.0144 | 0.1793 | 0.1946 |
| Air | 1.7e-05 | 0.0002 | 0.0002 |
| Plexiglass | 0.0107 | 0.2072 | 0.2187 |
| Aluminum | 0.2125 | 0.4274 | 0.6523 |

Figure 6A:
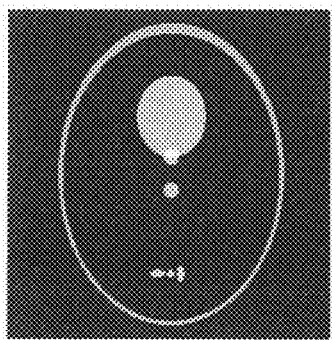
FIG. 6A is a model scan showing a simulated photoelectric component, $\phi$, according to one implementation of the disclosed system.
Figure 6B:
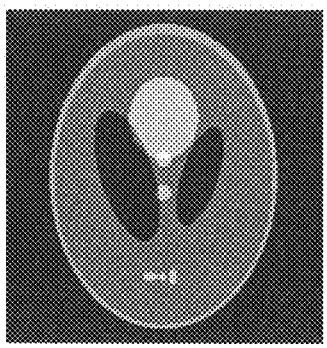
FIG. 6B is a model scan showing a simulated Compton scatter component $\theta$, according to one implementation of the disclosed system.
Figure 6C:
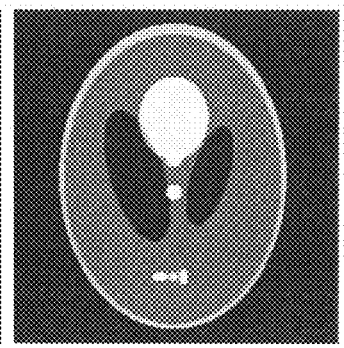
FIG. 6C is a model scan showing a reconstructed attenuation coefficient $\mu$, according to an implementation of the disclosed system.
Figure 6D:
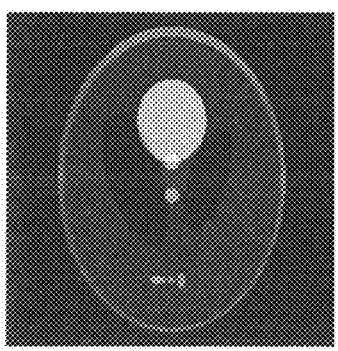
FIG. 6D, is a model scan showing a reconstructed photoelectric component, $\phi$, according to an implementation of the disclosed system.
Figure 6E:
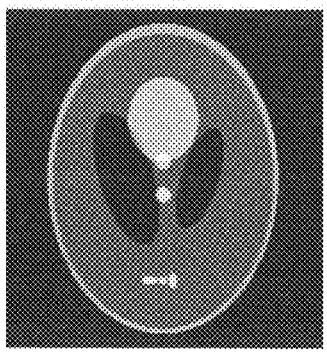
FIG. 6E is a model scan showing a reconstructed Compton scatter component, $\theta$, according to an implementation of the presently disclosed system.

As best shown in FIGS. 6C-6F, the attenuation coefficients of the example phantom can be clearly reconstructed using the presently-disclosed system and algorithm using a single scan. FIGS. 6A-6F depict the reconstructed images from the example phantom as follows. In FIG. 6A, simulated φ; in FIG. 6B, simulated θ; in FIG. 6C reconstructed μ using our proposed method; in FIG. 6D, reconstructed φ using our proposed method; in FIG. 6E, reconstructed θ using our proposed method; in FIG. 6F, reconstructed μ using the TV minimization by split Bregman (TV-SB).

To further validate the disclosed CT system and method, profiles of the 64th row of the reconstructed φ and θ of the example phantom are plotted in FIGS. 8A-8B. It can be observed that each of the reconstructed φ and θ components are very close to those of the corresponding phantoms. In FIGS. 8(a)-8(b), the profile is very steady and close to the recorded data.

To validate the disclosed method quantitatively, the mean square error ("MSE") was calculated by:

$$MSE = \frac{1}{N}\sum_{i=1}^{m}\sum_{j=1}^{n}(f_{ij}-\hat{f}_{ij})^2$$

where N is the total pixel number, f and $\hat{f}$ are the pixel values of the reconstructed image and the true image respectively.

FIGS. 7A-7B show the MSE for the simulated φ (FIG. 7A) and θ (FIG. 7B) against the number of iterations. From FIGS. 7A-B, it is apparent that the MSE decreases very quickly to a small value, and it then decreases further slowly, which implies that the presently-disclosed algorithm converges to a stable solution. The number of iterations can be increased to get larger peak signal to noise ratios of reconstructed φ and θ and smaller mean square errors ("MSEs"), as well as bring the profiles of reconstructed φ and θ be much closer to the simulated φ (FIG. 7A) and θ (FIG. 7B).

However, the visual difference is barely observable in the reconstructed images. Therefore, as would be apparent to a skilled artisan, in various implementations the process can be halted after a sufficient number of iterations have been run without significant loss of accuracy. The example of FIGS. 11A-11D and 12A-D demonstrates the intermediate reconstruction results during the iterations.

Returning to FIGS. 6A-F, the presently disclosed results demonstrate the advantage of the disclosed algorithm over prior art algorithms directed to the reconstruction of spectral-independent attenuation coefficients. In particular, the presently disclosed method and system can be compared with the total variation ("TV") minimization and a linear CT scan model as follows:

$$\min_{\mu} \lambda TV(\mu) + \frac{1}{2}\|A\mu - y\|^2_{L_2(\Omega)} \quad (18)$$

where $\mu$ is the spectral-independent attenuation coefficients, and $TV(\mu)=\| |\nabla\mu| \|_1$ with $|\nabla\mu|=\sqrt{\mu_x^2+\mu_y^2}$ is the total variation.

Figure 6F:
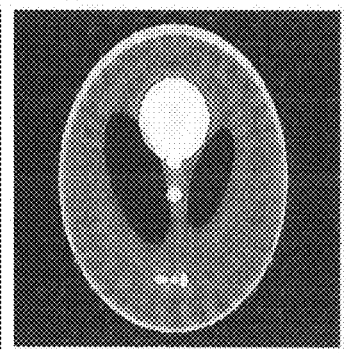
FIG. 6F is a model scan showing a reconstructed attenuation coefficient, $\mu$, using the TV minimization by split Bregman (TV-SB) of a further implementation of the disclosed method.

In (18), the operator A is the linear system matrix. A split Bregman algorithm can be used to solve (18). This can be referred to as the TV minimization by split Bregman ("TV-SB"). The reconstruction results by TV-SB use the same projection views as those in the disclosed method. The results of TV-SB method are shown in FIG. 6F. From FIG. 6F, it can be observed that there are still many obvious artifacts in the reconstructed images. This result is validated further in FIG. 8C where it can be observed that the profile of the TV-SB method is not very steady, and shows many oscillations.

In contrast, the presently-disclosed process yields steadier and more accurate results than the TV-SB method, which are correspondingly more accurate approximations of the observed data. Consequently, the presently-disclosed system yields many improvements as compared with the TV-SB method.

B. Example II: Sheep Head

To further assess the capacity of the presently-disclosed system, a sheep's head was scanned using cone-beam imaging geometry, as described previously. The distances from the X-ray source to the rotation center and the detector are 109.76 cm and 139.83 cm respectively. 1195 projections were collected under a fast-continuous-rotation scanning mode. The effective projection sequence used for reconstruction was extracted with a structure similarity ("SSIM") based-method. Among the final effective projection sequence, 200 equispaced projections were used for reconstruction. The presently disclosed system and algorithm was utilized to reconstruct the central slice with 200 projection views. After the rotation center was located, two 512×512 components were reconstructed and used to obtain spectral images at any energy according to Eq. (9).

Figures 9A, 9B, 9C:
FIG. 9A depicts a further reconstructed photoelectric component $\phi$.
FIG. 9B depicts the reconstructed attenuation coefficient $\mu(r,E)$ at monochromatic 70 keV.
FIG. 9C depicts a reconstructed attenuation coefficient, $\mu$, using the TV minimization by split Bregman (TV-SB) of a further implementation of the disclosed method.
Figure 9D:
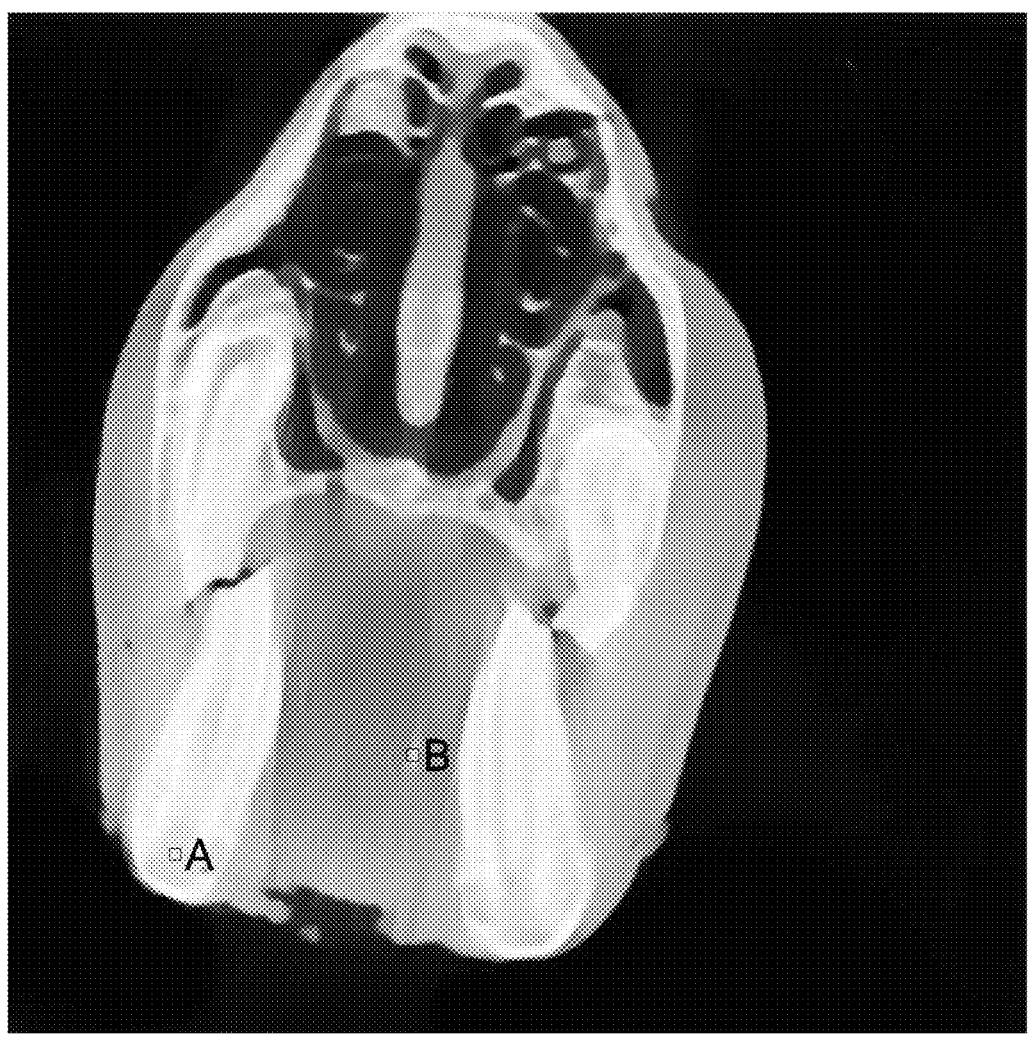
FIG. 9D depicts the $\mu(r,E)$ with color overlay by $\mu(r,E)$ at monochromatic 40 keV, 70 keV and 100 keV.

In the example of FIGS. 9A-D, a 101 spectra X-ray was used at 110 kV (as was shown above in FIG. 5) from 20 keV to 120 keV. In this example, 500 iterations were taken, with step sizes for $\phi$ and $\theta$ of 0.5 and 1.5, respectively. The reconstructed photoelectric component $\phi$ is shown in FIG. 9A, the reconstructed attenuation coefficient $\mu(r,E)$ at monochromatic 70 keV is shown in FIG. 9B, and the $\mu(r,E)$ with color overlay by $\mu(r,E)$ at monochromatic 40, 70, 100 keV is shown in FIG. 9D. A real color CT image was observed using just one scan, which is a principle advantage of the presently disclosed systems and methods. For example, regions A and B in FIG. 9B appear to have indistinguishable gray levels. However, in FIG. 9D, different colors can be observed. And the reconstructed $\phi$ in FIG. 9(a) displays greater detail than that in the reconstructed $\mu$ in FIG. 9B from gray levels, and greater details can be observed in FIG. 9D.

The presently disclosed system and method as shown in FIG. 9B can also be compared with the TV-SB method, which is depicted in FIG. 9C. In FIG. 9C obvious artifacts can be observed, especially in the top and near the boundary. Further, FIG. 9C also has insufficient detail, such as the black dot which can be observed in the lower left portion of the image.

Figure 10:
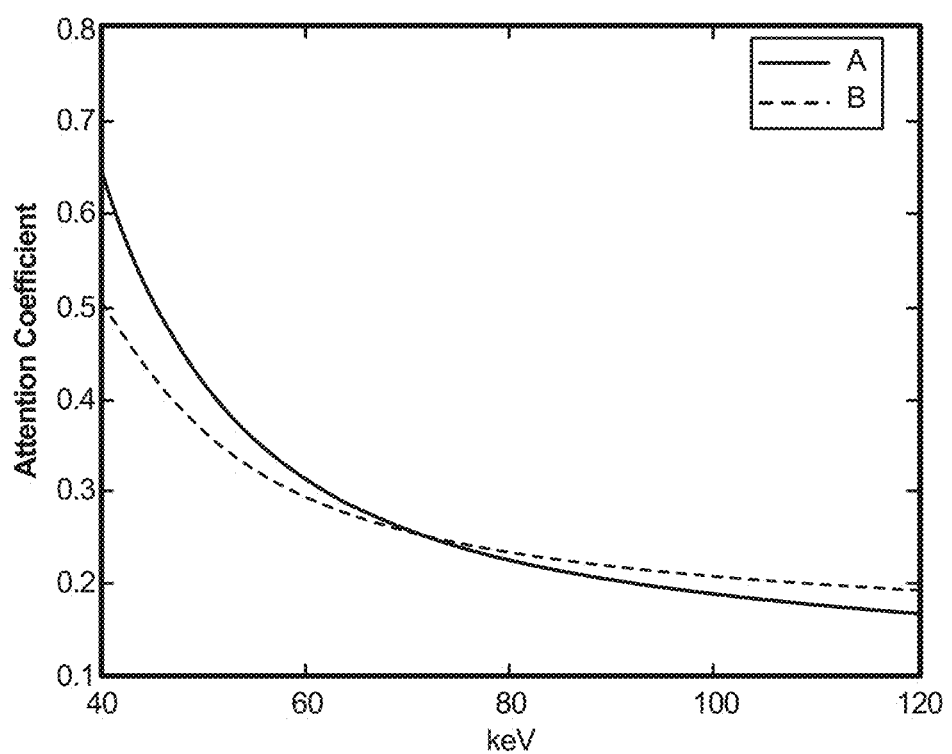
FIG. 10 depicts the spectral curves of the attenuation coefficient $\mu(r,E)$ from the implementations of FIGS. 9B and 9D.

To further demonstrate the advantages of the disclosed spectral CT reconstruction algorithm, system and methods, in FIGS. 9B and 9D, spectral curves of the attenuation coefficient $\mu(r,E)$ can be drawn at two points, designated as regions A and B, respectively. As best shown in FIG. 10, these spectral curves clearly differentiate the spectral nature of the two regions (designated by A and B). The spectral curves produced by the present algorithm can therefore provide a valuable tool in analyzing and diagnosing the nature of a tumor, such as the fat content, malignancy and other known factors in the art.

Figure 12A:
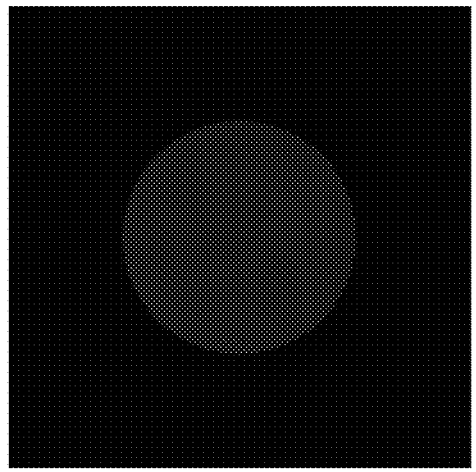
FIG. 12A depicts a reconstructed attenuation coefficients $\mu(r,E)$ with an overlay for interior spectral CT at monochromatic E=40, 70, 100 keV for 1 iteration, according to one embodiment.
Figure 12B:
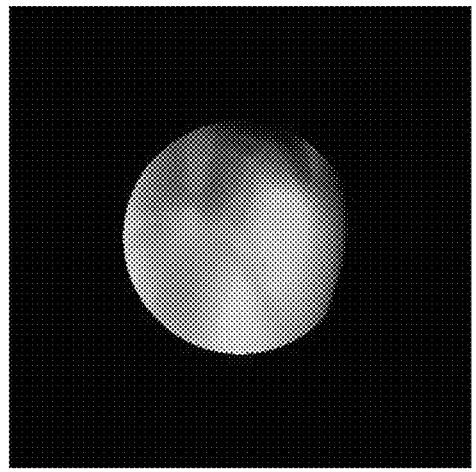
FIG. 12B depicts a reconstructed attenuation coefficients $\mu(r,E)$ with an overlay for interior spectral CT at monochromatic E=40, 70, 100 keV for 10 iterations, according to one embodiment.
Figure 12C:
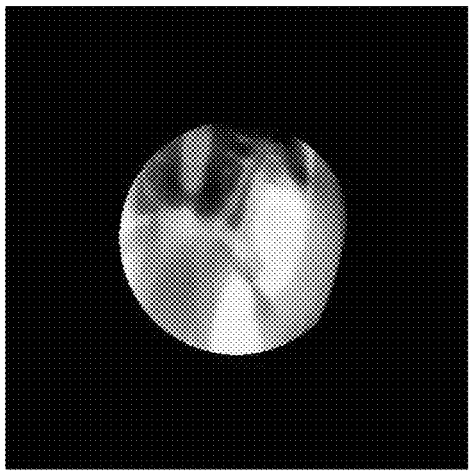
FIG. 12C depicts a reconstructed attenuation coefficients μ(r,E) with an overlay for interior spectral CT at monochromatic E=40, 70, 100 keV for 40 iterations, according to one embodiment.
Figure 12D:
FIG. 12D depicts a reconstructed attenuation coefficients μ(r,E) with an overlay for interior spectral CT at monochromatic E=40, 70, 100 keV for 500 iterations, according to one embodiment.

FIGS. 11A-11D depict reconstructed attenuation coefficients $\mu(r,E)$ with an overlay for global spectral CT, and FIGS. 12A-12D depict reconstructed attenuation coefficients $\mu(r,E)$ with an overlay for interior spectral CT at monochromatic E=40, 70, 100 keV for 1 iteration (FIG. 12A); at 10 iterations (FIG. 12B); at 40 iterations (FIG. 12C) and at 500 iterations (FIG. 12D).

In summary, the present disclosure includes a framelet-based iterative algorithm for polychromatic CT which can reconstruct two components using a single scan, as shown in FIGS. 6(D-6E. Excellent results were obtained in simulations with synthesized and real-world data, as shown in FIGS. 6A-9D. It is also shown that the present algorithm and system can prevent both beam-hardening and metal streak artifacts effectively.

C. Example III: SVD-Based Method

To further assess the capacity of the presently-disclosed system, in experiment with synthesized data, the Shepp-Logan Phantom was used with a fan-beam imaging geometry, which is similar to the one used above. In this system, the radius of the circular scanning locus is 57 cm, and for whole reconstruction the diameter of the FOV is 22.4 cm corresponding to 672 detector bins, with each element 0.033 cm. The reconstructed images are of size 128×128, with each pixel size 0.15625×0.15625 and reconstructed by our framelet-based three-step iterative reconstruction from 30 projection views.

This example used 21 spectra of X-ray at 110 kV from 20 keV to 120 keV. The photon number is approximately $1.3\times10^6$. The run comprised 2000 iterations, and the step sizes of $\phi$ and $\theta$ were 0.4 and 0.9 respectively.

Using 101 $\mu(r,E)$ at energies between 20 keV and 120 keV, a true color CT image was obtained by the color fusion method based on SVD discussed in relation to Eqs. XX-8-XX-7), and the results are shown in FIGS. 13A (showing the iterative framelet method) and 13B (using the SVD-based method.

As is apparent from FIGS. 13A-13B, one can see that the color image using the framelet method (FIG. 13A) is more continuous than that using SVD (FIG. 13B). But it is easier to differentiate different regions in the color image by SVD (FIG. 13B). Accordingly, either method may be preferable in certain implementations.

To further assess the method using real data, a further analysis on a sheep's head (as described above) was performed. In this example, the distances from the X-ray source to the rotation center and the detector were 109.76 cm and 139.83 cm respectively. For interior reconstructions using the framelet-based three-step iterative reconstruction, 200 projections were collected, corresponding to 513 detector bins.

In this example, 21 spectra of X-ray were used at 110 kV from 20 keV to 120 keV. The photon number is approximately $1.3\times10^6$. 300 iterations were taken, at step sizes for $\phi$ and $\theta$ were 0.5 and 1.5 respectively. Using the reconstruction algorithm, it is possible to obtain any spectral images $\mu(r,E)$ at any energy according to Eq. (2).

Using 101 μ(r,E) at energies between 20 keV to 120 keV, it is again possible to obtain obtain a true color CT image of size 170×170, which is part of the reconstructed 512×512 images reconstructed in [2], by the color fusion method based on SVD introduced in section 2.2.

The color images by the framlet method and the SVD method are shown in FIGS. 14A and 14B, respectively. As would be understood by one of skill in the art, is easier to differentiate different regions in the color image by SVD. Accordingly, either method may be preferable in certain implementations.

Accordingly, using the reconstructed images with spectral information, it is possible to obtain true color images based on singular value decomposition method, which is preferable to methods using manually choosen images corresponding to three different energies as RGB components. It is possible to obtain a true color CT image that can differentiate very small materials in the object.

Although the disclosure has been described with reference to preferred embodiments, persons skilled in the art will recognize that changes may be made in form and detail without departing from the spirit and scope of the disclosed apparatus, systems and methods.

What is claimed is:

1. A single scan polychromatic CT image reconstruction system, comprising:
  a. a non-transitory computer-readable media coupled to a computer storing a single CT scan; and
  b. a processor configured to implement a framlet-based iterative algorithm for CT image reconstruction from the single CT scan and a color reconstruction step, the iterative algorithm iterating on n comprising:
    i. a scaled-gradient descent step of constant or variant step sizes:

$$\phi_j^{n+\frac{1}{3}} = \phi_j^n - \delta_1 \frac{\partial L}{\partial \phi_j}(\phi^n, \theta^n) \left( \sum_{h=1}^{J} \left( \frac{\partial^2 L}{\partial \phi_j \partial \phi_h} + \frac{\partial^2 L}{\partial \phi_j \partial \theta_h} \right)(\phi^n, \theta^n) \right)^{-1},$$

$$\theta_j^{n+\frac{1}{3}} = \theta_j^n - \delta_2 \frac{\partial L}{\partial \theta_j}(\phi^n, \theta^n) \left( \sum_{h=1}^{J} \left( \frac{\partial^2 L}{\partial \theta_j \partial \phi_h} + \frac{\partial^2 L}{\partial \theta_j \partial \theta_h} \right)(\phi^n, \theta^n) \right)^{-1};$$

ii. a non-negativity step:

$$\phi_j^{n+\frac{2}{3}} = \max\left\{\phi_j^{n+\frac{1}{3}}, 0\right\},$$

$$\theta_j^{n+\frac{2}{3}} = \max\left\{\theta_j^{n+\frac{1}{3}}, 0\right\}; \text{ and}$$

iii. a soft thresholding step:

$$\phi_j^{n+1} = \mathcal{W}^T T_{\lambda_1}\left(\mathcal{W}\phi_j^{n+\frac{2}{3}}\right),$$

$$\theta_j^{n+1} = \mathcal{W}^T T_{\lambda_2}\left(\mathcal{W}\theta_j^{n+\frac{2}{3}}\right);$$

wherein the processor is configured to reconstruct the CT image following the execution of iterative steps i-iii until a stop criterion is met and the color reconstruction step is subsequently performed, and wherein:
  i. vectors $\phi^n=(\phi_j^n)$, $\phi^{n+1/3}=(\phi_j^{n+1/3})$, and $\phi^{n+2/3}=(\phi_j^{n+2/3})$ define a photoelectric component, and
  ii. vectors $\theta^n=(\theta_j^n)$, $\theta^{n+1/3}=(\theta_j^{n+1/3})$, and $\theta^{n+2/3}=(\theta_j^{n+2/3})$ define a Compton scatter component of the attenuation coefficient μ(r,E) at each point r indexed by j,
  iii. $\mathcal{W}$ is an operator for transferring $\phi_j^{n+2/3}$ and $\theta_j^{n+2/3}$ to the framlet domain,
  iv. $T_{\lambda_1}$ and $T_{\lambda_2}$ are self-thresholding operators, and
  v. $\mathcal{W}^T$ is an operator for transferring sparsified coefficients back to the (φ,θ) domain.

2. The system of claim 1, wherein the soft thresholding step comprises constant or variant thresholding sizes.

3. The system of claim 1, wherein the scaled-gradient descent step comprises constant or variant step sizes.

4. The system of claim 1, further comprising a CT platform.

5. The system of claim 1, wherein the soft thresholding step is configured to promote sparsity in the framlet domain.

6. The system of claim 1, wherein the during non-negativity step, any negative components are set to 0 to maintain positivity of attenuation coefficients (φ,θ).

7. The system of claim 1, wherein the color reconstruction step further comprises an adaptive color fusion method.

8. The system of claim 1, wherein the reconstructed CT image is interior spectral CT.

9. The system of claim 1, wherein the reconstructed CT image is global spectral CT.

10. The system of claim 1, wherein the iterative algorithm comprises setting initial value $\phi_j^0, \theta_j^0$ for $\phi_j^n, \theta_j^n$.

11. The system of claim 1, wherein the adaptive color fusion method is based on a singular value decomposition.

12. The system of claim 1, further comprising a tight frame system with wavelet structure.

13. The system of claim 1, further comprising a CT platform configured to generate a single polychromatic scan.

14. The system of claim 1, wherein the stop criterion comprises a fixed number of iterations or stability of the resulting vectors $\phi^n$ and $\theta^n$.

* * * * *